(12) United States Patent
Schelwies et al.

(10) Patent No.: US 10,301,244 B2
(45) Date of Patent: *May 28, 2019

(54) METHOD FOR SYNTHESIZING OPTICALLY ACTIVE CARBONYL COMPOUNDS

(71) Applicant: BASF SE, Ludwigshafen Am Rhein (DE)

(72) Inventors: Mathias Schelwies, Heidelberg (DE); Rocco Paciello, Ludwigshafen (DE); Gunnar Heydrich, Limburgerhof (DE); Günter Wegner, Römerberg (DE); Gerd-Dieter Tebben, Mannheim (DE); Martin Haubner, Eppelheim (DE); Andreas Keller, Speyer (DE); Oliver Bey, Niederkirchen (DE); Stephanie Renz, Schwetzingen (DE); Georg Seeber, Lambsheim (DE)

(73) Assignee: BASF SE (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/964,400

(22) Filed: Apr. 27, 2018

(65) Prior Publication Data

US 2018/0244598 A1    Aug. 30, 2018

Related U.S. Application Data

(63) Continuation of application No. 15/536,524, filed as application No. PCT/EP2015/080392 on Dec. 18, 2015, now Pat. No. 9,975,837.

(30) Foreign Application Priority Data

Dec. 19, 2014 (EP) ..................................... 14199410

(51) Int. Cl.
    C07C 45/50    (2006.01)
    C07C 45/62    (2006.01)
    C07C 29/17    (2006.01)
    C07C 29/56    (2006.01)

(52) U.S. Cl.
    CPC ............ *C07C 45/62* (2013.01); *C07C 29/172* (2013.01); *C07C 29/56* (2013.01); *C07B 2200/07* (2013.01); *C07C 2601/14* (2017.05)

(58) Field of Classification Search
    CPC ..... C07C 45/50; C07C 45/62; C07C 2601/14; C07B 2260/07
    See application file for complete search history.

(56) References Cited

U.S. PATENT DOCUMENTS 4,237,072 A    12/1980  Aviron-Violet et al.
6,838,061 B1    1/2005  Berg et al.
7,534,921 B2    5/2009  Jäkel et al.
(Continued)

FOREIGN PATENT DOCUMENTS

EP    0000315 A1    1/1979
EP    1140349 A1    10/2001
EP    1225163 A2    7/2002
(Continued)

OTHER PUBLICATIONS

Chapuis, C., et al., "Synthesis of Citronellal by Rh1-Catalysed Asymmetric Isomerization of N,N-Diethyl-Substituted Geranyl- and Nerylamines or Geraniol and Nerol in the Presence of Chiral Diphosphino Ligands, under Homogeneous and Supported Conditions", Helvetica Chimica Acta, vol. 84, (2001), pp. 230-242.

Dang, T-P., et al., "Catalysis of Homogeneous Phase Hydrogenation of ?-? Unsaturated Aldehydes. Application to the Asymmetric Synthesis of Citronellal", Journal of Molecular Catalysis, vol. 16, (1982), pp. 51-59.

International Search Report for PCT/EP2015/080392 dated Mar. 8, 2016.

(Continued)

*Primary Examiner* — Sikarl A Witherspoon
(74) *Attorney, Agent, or Firm* — Drinker Biddle & Reath LLP

(57) ABSTRACT

The present invention relates to a process for the preparation of an optically active carbonyl compound by asymmetric hydrogenation of a prochiral α,β-unsaturated carbonyl compound with hydrogen in the presence of at least one optically active transition metal catalyst that is soluble in the reaction mixture and which has rhodium as catalytically active transition metal and a chiral, bidentate bisphosphine ligand, wherein the reaction mixture during the hydrogenation of the prochiral α,β-unsaturated carbonyl compound additionally comprises at least one compound of the general formula (I):

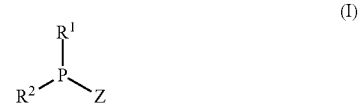

in which $R^1$, $R^2$: are identical or different and are $C_6$- to $C_{10}$-aryl which is unsubstituted or carries one or more, e.g. 1, 2, 3, 4 or 5, substituents which are selected from $C_1$- to $C_6$-alkyl, $C_3$- to $C_6$-cycloalkyl, $C_6$- to $C_{10}$-aryl, $C_1$- to $C_6$-alkoxy and amino;

Z is a group $CHR^3R^4$ or aryl which is unsubstituted or carries one or more, e.g. 1, 2, 3, 4 or 5, substituents which are selected from $C_1$- to $C_6$-alkyl, $C_3$- to $C_6$-cycloalkyl, $C_6$- to $C_{10}$-aryl, $C_1$- to $C_6$-alkoxy and amino, wherein $R^3$ and $R^4$ are as defined in the claims and the description.

14 Claims, No Drawings

(56) References Cited

U.S. PATENT DOCUMENTS 7,973,198 B2     7/2011    Schrnidt-Leithoff et al.

FOREIGN PATENT DOCUMENTS

| JP | S5278812 A | 7/1977 |
| WO | WO-0030743 A1 | 6/2000 |
| WO | WO-2006040096 A1 | 4/2006 |
| WO | WO-2008132057 A1 | 11/2008 |

OTHER PUBLICATIONS

"Saturated aldehydes selective prodn.—by treating unsaturated aldehyde with hydrogen and carbon monoxide, using catalyst, tertiary phosphine and amine", WPI/Derwent Accession No. 1977-58267Y, XP-002364613, Jul. 2, 1977.

Written Opinion of the International Searching Authority for PCT/EP2015/080392 dated Mar. 8, 2016.

METHOD FOR SYNTHESIZING OPTICALLY ACTIVE CARBONYL COMPOUNDS

CROSS-REFERENCE TO RELATED APPLICATIONS

This application is a continuation application of U.S. application Ser. No. 15/536,524, filed Jun. 15, 2017, which is incorporated by reference in its entirety. U.S. application Ser. No. 15/536,524 is a national stage application (under 35 U.S.C. § 371) of PCT/EP2014/002031, filed Dec. 18, 2015, which claims benefit of European Application No. 14199410.3, filed Dec. 19, 2014, which is incorporated herein by reference in their entirety.

The present invention relates to a process for the preparation of an optically active carbonyl compound by asymmetric hydrogenation of a prochiral α,β-unsaturated carbonyl compound with hydrogen in the presence of at least one optically active transition metal catalyst that is soluble in the reaction mixture. Specifically, the present invention relates to a process for the preparation of optically active aldehydes or ketones, in particular citronellal, by asymmetric hydrogenation of the corresponding prochiral α,β-unsaturated aldehydes or ketones.

BACKGROUND OF THE INVENTION

Many optically active aldehydes and ketones are valuable intermediates in the synthesis of relatively highly refined chiral substances of value and active ingredients, or are already themselves valuable fragrances and aroma substances.

EP-A 0 000 315 relates to a process for the preparation of optically active citronellal by hydrogenation of geranial or neral in the presence of a catalyst complex composed of rhodium and a chiral phosphine which is dissolved in the reaction system.

In J. Mol. Cat., 1982, volume 16, pages 51-59, T.-P. Dang et al. describe a process for the homogeneous-catalytic hydrogenation of α,β-unsaturated aldehydes, and the application of this process for the preparation of optically active citronellal. The catalysts used here were complex compounds of a rhodium carbonyl compound and a chiral diphosphine.

In Helv. Chim. Acta, 2001, volume 84, pages 230-242, footnote 4, Chapuis et al. also mention the asymmetric hydrogenation of geranial or neral to give optically active citronellal in the presence of a catalyst of $Rh_4(CO)_{12}$ and (R,R)-chiraphos (2R, 3R)-2,3-bis(diphenylphosphino)butane.

One problem when carrying out (homogeneous-catalytic) reactions catalyzed by means of soluble catalysts consists in the often inadequate stability of the catalyst complexes used or of the catalytically active metal or transition metal complex compound which is formed therefrom. Against the background of the often high price of such catalysts or catalyst precursors, homogeneous-catalytic reactions with complex transition metal catalysts can only be applied on an industrial scale in an economical manner in specific cases.

JP-A 52078812 describes a process for the hydrogenation of α,β-unsaturated aldehydes such as crotonaldehyde, cinnamaldehyde or α-methylcinnamaldehyde over homogeneous Rh catalysts under hydroformylation conditions in the presence of a triarylphosphine, a tertiary amine in stoichiometric amount and carbon monoxide.

WO 2006/040096 describes a process for the preparation of optically active carbonyl compounds by asymmetric hydrogenation of α,β-unsaturated carbonyl compounds with hydrogen in the presence of an optically active transition metal catalyst that is soluble in the reaction mixture and which has at least one carbon monoxide ligand and is characterized in that the catalyst is pretreated with a gas mixture comprising carbon monoxide and hydrogen and/or the asymmetric hydrogenation is carried out in the presence of carbon monoxide additionally introduced into the reaction mixture.

WO 2008/132057 likewise describes a process for the preparation of optically active carbonyl compounds by asymmetric hydrogenation of α,β-unsaturated carbonyl compounds which is based on the process disclosed in WO 2006/040096. To better control the carbon monoxide concentration in the reaction mixture during the hydrogenation, this process additionally includes the measures that the pretreatment of the catalyst precursor is carried out with a gas mixture comprising 20 to 90% by volume carbon monoxide, 10 to 80% by volume hydrogen and 0 to 5% by volume further gases, where the specified volume fractions add up to 100% by volume, at a pressure of 5 to 100 bar, excess carbon monoxide is separated off from the catalyst obtained in this way prior to use in the asymmetric hydrogenation, and the asymmetric hydrogenation is carried out in the presence of hydrogen with a carbon monoxide content of from 100 to 1200 ppm.

Particularly in the case of the last-mentioned processes for the asymmetric hydrogenation of α,β-unsaturated carbonyl compounds, it was possible to considerably improve the stability and/or the service life of the catalyst complexes used or of the catalytically active metal or transition metal complex compound which forms therefrom compared with conventional processes. On account of moderate and fluctuating catalyst activities, the said processes are in need of improvement as regards their conversion rates, particularly if they are carried out on an industrial scale.

SUMMARY OF THE INVENTION

It was an object of the present invention to provide an improved process for the homogeneous-catalytic asymmetric hydrogenation of α,β-unsaturated aldehydes or ketones which is distinguished by an improved catalyst activity coupled with simultaneously high enantiomers selectivity in order to achieve high conversion rates with high product selectivity. Furthermore, the catalytic system should be distinguished by a high stability and thus by an increased service life of the catalytically active transition metal complex compound to be used in optically active form. The process should as a result be suitable to a particular degree for applications on an industrial scale.

Surprisingly, it has been found that the catalytic activity of the optically active transition metal catalysts used for the homogeneous-catalytic asymmetric hydrogenation of prochiral α,β-unsaturated carbonyl compounds, which comprise rhodium as catalytically active transition metal, can be significantly increased by adding a phosphine compound of the general formula (I), as defined below, without adversely affecting their stability and selectivity in a significant manner.

The present invention therefore relates to a process for the preparation of an optically active carbonyl compound by asymmetric hydrogenation of a prochiral α,β-unsaturated carbonyl compound with hydrogen in the presence of at least one optically active transition metal catalyst that is soluble in the reaction mixture and which has rhodium as catalytically active transition metal and a chiral, bidentate bisphosphine ligand, wherein the reaction mixture during the hydrogenation of the prochiral α,β-unsaturated carbonyl compound additionally comprises at least one compound of the general formula (I):

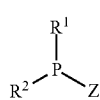
(I)

in which
R¹, R²: are identical or different and are $C_6$- to $C_{10}$-aryl which is unsubstituted or carries one or more, e.g. 1, 2, 3, 4 or 5, substituents which are selected from $C_1$- to $C_6$-alkyl, $C_3$- to $C_6$-cycloalkyl, $C_6$- to $C_{10}$-aryl, $C_1$- to $C_6$-alkoxy and amino;
Z is a group $CHR^3R^4$ or aryl which is unsubstituted or carries one or more, e.g. 1, 2, 3, 4 or 5, substituents which are selected from $C_1$- to $C_6$-alkyl, $C_3$- to $C_6$-cycloalkyl, $C_6$- to $C_{10}$-aryl, $C_1$- to $C_6$-alkoxy and amino, in which
R³ is $C_1$- to $C_4$-alkyl, $C_1$- to $C_4$-alkoxy-$C_1$- to $C_4$-alkyl, $C_3$- to $C_6$-cycloalkyl or $C_6$- to $C_{10}$-aryl, where one or two nonadjacent $CH_2$ groups in $C_3$- to $C_6$-cycloalkyl can also be replaced by one or two oxygen atoms;
R⁴ is $C_1$- to $C_4$-alkyl which is unsubstituted or carries a group $P(=O)R^{4a}R^{4b}$, $C_1$- to $C_4$-alkoxy, $C_1$- to $C_4$-alkoxy-$C_1$- to $C_4$-alkyl, $C_3$- to $C_6$-cycloalkyl or $C_6$- to $C_{10}$-aryl, where one or two nonadjacent $CH_2$ groups in $C_3$- to $C_6$-cycloalkyl can also be replaced by an oxygen atom, and where $C_3$- to $C_6$-cycloalkyl and $C_6$- to $C_{10}$-aryl are unsubstituted or carry one or more, e.g. 1, 2, 3, 4 or 5, substituents which are selected from $C_1$- to $C_4$-alkyl, $C_1$- to $C_4$-alkoxy and amino;
or
R³, R⁴: together with the carbon atom to which they are bonded, are $C_4$- to $C_8$-cycloalkyl, in which one or two nonadjacent $CH_2$ groups in $C_3$- to $C_6$-cycloalkyl can also be replaced by one or two oxygen atoms and where $C_3$- to $C_6$-cycloalkyl is unsubstituted or carries one or more, e.g. 1, 2, 3, 4 or 5, substituents which are selected from $C_1$- to $C_4$-alkyl, $C_1$- to $C_4$-alkoxy and A-P(=O)$R^{4a}R^{4b}$,
where A is a chemical bond or a $C_1$- to $C_4$-alkylene; and
$R^{4a}$, $R^{4b}$ are identical or different and are phenyl which is unsubstituted or carries one or more substituents which are selected from $C_1$- to $C_6$-alkyl, $C_3$- to $C_6$-cycloalkyl, $C_6$- to $C_{10}$-aryl, $C_1$- to $C_6$-alkoxy and amino.

Specifically, the present invention relates to a process for the preparation of optically active aldehydes or ketones, in particular citronellal, by asymmetric hydrogenation of the corresponding prochiral α,β-unsaturated aldehydes or ketones.

DETAILED DESCRIPTION OF THE INVENTION

The process according to the invention is suitable for the preparation of optically active carbonyl compounds such as aldehydes, ketones, esters, lactones or lactams by asymmetric, i.e. enantioselective, hydrogenation of the corresponding carbonyl compounds which have an ethylenic double bond in α,β position relative to the carbonyl group. According to the invention, the ethylenic double bond in the α,β position relative to the carbonyl group is hydrogenated in the presence of an optically active transition metal catalyst that is soluble in the reaction mixture and which comprises rhodium as catalytically active transition metal, as well as a phosphine compound of the general formula (I) to give a carbon-carbon single bond, wherein the tetrahedral carbon atom newly provided in the β position carries four different substituents and is obtained in non-racemic form. Accordingly, in the context of the present invention, the term asymmetric hydrogenation is to be understood as meaning a hydrogenation during which the two enantiomeric forms of the hydrogenation product are not obtained in equal parts.

In the definitions of the variables given in the formulae above and below, collective terms are used which are generally representative of the respective substituents. The meaning $C_n$- to $C_m$- indicates the respective possible number of carbon atoms in the particular substituents or substituent moiety.

In the context of the present invention, the expression "alkyl" comprises unbranched or branched alkyl groups having 1 to 4, 6, 12 or 25 carbon atoms. These include, for example, $C_1$- to $C_6$-alkyl, such as methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl and the like. Preferably "alkyl" is unbranched or branched $C_1$- to $C_6$-alkyl groups.

In the context of the present invention, the expression "cycloalkyl" comprises cyclic, saturated hydrocarbon groups having 3 to 6, 12 or 25 carbon ring members, e.g. $C_3$-$C_6$-cycloalkyl such as cyclopropyl, cyclobutyl, cyclopentyl, cyclohexyl, cycloheptyl and cyclooctyl, or $C_7$-$C_{12}$-bicycloalkyl.

In the context of the present invention, the expression "alkoxy" is an alkyl group having 1 to 6 carbon atoms bonded via an oxygen, e.g. $C_1$- to $C_6$-alkoxy, such as methoxy, ethoxy, n-propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. Preferably, "alkoxy" is $C_1$- to $C_4$-alkoxy.

In the context of the present invention, the expression "alkenyl" comprises unbranched or branched hydrocarbon radicals having 2 to 4, 6, 12 or 25 carbon atoms which comprise at least one double bond, for example 1, 2, 3 or 4 double bonds. These include, for example, $C_2$-$C_6$-alkenyl such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl. Preferably, "alkenyl" is unbranched $C_2$- to $C_{12}$-alkenyl groups or branched $C_3$- to $C_{12}$-alkenyl groups having in each case 1 to 3 double bonds, particularly preferably unbranched $C_2$- to $C_6$-alkenyl groups or branched $C_3$- to $C_6$-alkenyl groups having in each case one double bond.

In the context of the present invention, the expression "alkylene" refers to divalent hydrocarbon radicals having 2 to 25 carbon atoms. The divalent hydrocarbon radicals can be unbranched or branched. These include, for example, $C_2$-$C_{16}$-alkylene groups, such as 1,4-butylene, 1,5-pentylene, 2-methyl-1,4-butylene, 1,6-hexylene, 2-methyl-1,5-pentylene, 3-methyl-1,5-pentylene, 1,7-heptylene, 2-methyl-1,6-hexylene, 3-methyl-1,6-hexylene, 2-ethyl-1,5-pentylene, 3-ethyl-1,5-pentylene, 2,3-dimethyl-1,5-pentylene, 2,4-dimethyl-1,5-pentylene, 1,8-octylene, 2-methyl-1,7-heptylene, 3-methyl-1,7-heptylene, 4-methyl-1,7-heptylene, 2-ethyl-1,6-hexylene, 3-ethyl-1,6-hexylene, 2,3-dimethyl-1,6-hexylene, 2,4-dimethyl-1,6-hexylene, 1,9-nonylene, 2-methyl-1,8-octylene, 3-methyl-1,8-octylene, 4-methyl-1,8-octylene, 2-ethyl-1,7-heptylene, 3-ethyl-1,7-heptylene, 1,10-decylene, 2-methyl-1,9-nonylene, 3-methyl-1,9-nonylene, 4-methyl-1,9-nonylene, 5-methyl-1,9-nonylene, 1,11-undecylene, 2-methyl-1,10-decylene, 3-methyl-1,10-decylene, 5-methyl-1,10-decylene, 1,12-dodecylene, 1,13-tridecylene, 1,14-tetradecylene, 1,15-pentadecylene, 1,16-hexadecylene and the like. Preferably, "alkylene" is unbranched $C_2$- to $C_{12}$-alkylene groups or branched $C_3$- to $C_{12}$-alkylene groups, in particular unbranched $C_2$- to $C_6$-alkylene groups or branched $C_3$- to $C_6$-alkylene groups.

In the mono- or polybranched or substituted alkylene groups, the carbon atom at the branching point or the carbon atoms at the respective branching points or the carbon atoms carrying a substituent can have, independently of one another, a R or S configuration or both configurations in equal or different proportions.

In the context of the present invention, the expression "alkenylene" refers to divalent hydrocarbon radicals having 2 to 25 carbon atoms, which can be unbranched or branched, where the main chain has one or more double bonds, for example 1, 2 or 3 double bonds. These include, for example, $C_2$- to $C_{18}$-alkenylene groups, such as ethylene, propylene, 1-, 2-butylene, 1-, 2-pentylene, 1-, 2-, 3-hexylene, 1,3-hexadienylene, 1,4-hexadienylene, 1-, 2-, 3-heptylene, 1,3-heptadienylene, 1,4-heptydienylene, 2,4-heptadienylene, 1-, 2-, 3-octenylene, 1,3-octadienylene, 1,4-octadienylene, 2,4-octadienylene, 1-, 2-, 3-nonenylene, 1-, 2-, 3-, 4-, 5-decenylene, 1-, 2-, 3-, 4-, 5-undecenylene, 2-, 3-, 4-, 5-, 6-dodecenylene, 2,4-dodecadienylene, 2,5-dodecadienylene, 2,6-dodecadienylene, 3-, 4-, 5-, 6-tridecenylene, 2,5-tridecadienylene, 4,7-tridecadienylene, 5,8-tridecadienylene, 4-, 5-, 6-, 7-tetradecenylene, 2,5-tetradecadienylene, 4,7-tetradecadienylene, 5,8-tetradecadienylene, 4-, 5-, 6-, 7-pentadecenylene, 2,5-pentadecadienylene, 4,7-pentadecadienylene, 5,8-pentadecadienylene, 1,4,7-pentadecatrienylene, 4,7,11-pentadecatrienylene, 4,6,8-pentadecatrienylene, 4-, 5-, 6-, 7-, 8-hexadecenylene, 2,5-hexadecadienylene, 4,7-hexadecadienylene, 5,8-hexadecadienylene, 2,5,8-hexadecatrienylene, 4,8,11-hexadecatrienylene, 5,7,9-hexadecatrienylene, 5-, 6-, 7-, 8-heptadecenylene, 2,5-heptadecadienylene, 4,7-heptadecadienylene, 5,8-heptadecadienylene, 5-, 6-, 7-, 8-, 9-octadecenylene, 2,5-octadecadienylene, 4,7-octadecadienylene, 5,8-octadecadienylene and the like. Preferably, "alkenylene" is unbranched $C_3$- to $C_{12}$-alkenylene groups or branched $C_4$- to $C_{12}$-alkenylene groups having in each case one or two double bonds, in particular unbranched $C_3$- to $C_8$-alkenylene groups with one double bond.

The double bonds in the alkenylene groups can be present independently of one another in the E and also in the Z configuration or as a mixture of both configurations.

In the context of the present invention, the expression "halogen" comprises fluorine, chlorine, bromine and iodine, preferably fluorine, chlorine or bromine.

In the context of the present invention, the expression "aryl" comprises a mono- to trinuclear aromatic ring system comprising 6 to 14 carbon ring members. These include, for example, $C_6$- to $C_{10}$-aryl, such as phenyl or naphthyl.

In the context of the present invention, the expression "hetaryl" comprises mono- to trinuclear aromatic ring system comprising 6 to 14 carbon ring members, where one or more, for example 1, 2, 3, 4, 5 or 6, carbon atoms are substituted by a nitrogen, oxygen and/or sulfur atom. These include, for example, $C_3$- to $C_9$-hetaryl groups, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 2-indolyl, 3-indolyl, 4-indolyl, 5-indolyl, 6-indolyl, 7-indolyl and the like. Preferably, "hetaryl" is $C_5$- to $C_6$-hetaryl.

In the context of the present invention, the expression "aralkyl" comprises a mono- to dinuclear aromatic ring system, comprising 6 to 10 carbon ring members, bonded via an unbranched or branched $C_1$- to $C_6$-alkyl group. These include, for example, $C_7$- to $C_{12}$-aralkyl, such as phenylmethyl, 1-phenylethyl, 2-phenylethyl, 1-phenylpropyl, 2-phenylpropyl, 3-phenylpropyl and the like.

In the context of the present invention, the expression "aralkyl" comprises mono- to dinuclear aromatic ring systems comprising 6 to 10 carbon ring members which is substituted with one or more, for example 1, 2 or 3, unbranched or branched $C_1$- to $C_6$-alkyl radicals. These include e.g. $C_7$- to $C_{12}$-alkylaryl, such as 1-methylphenyl, 2-methylphenyl, 3-methylphenyl, 1-ethylphenyl, 2-ethylphenyl, 3-ethylphenyl, 1-propylphenyl, 2-propylphenyl, 3-propylphenyl, 1-isopropylphenyl, 2-isopropylphenyl, 3-isopropylphenyl, 1-butylphenyl, 2-butylphenyl, 3-butylphenyl, 1-isobutylphenyl, 2-isobutylphenyl, 3-iso-butylphenyl, 1-sec-butylphenyl, 2-sec-butylphenyl, 3-sec-butylphenyl, 1-tert-butylphenyl, 2-tert-butylphenyl, 3-tert-butylphenyl, 1-(1-pentenyl) phenyl, 2-(1-pentenyl)phenyl, 3-(1-pentenyl)phenyl, 1-(2-pentenyl)phenyl, 2-(2-pentenyl)phenyl, 3-(2-pentenyl)phenyl, 1-(3-pentenyl)phenyl, 2-(3-pentenyl)phenyl, 3-(3-pentenyl)phenyl, 1-(1-(2-methylbutyl))phenyl, 2-(1-(2-methylbutyl))phenyl, 3-(1-(2-methylbutyl))phenyl, 1-(2-(2-methylbutyl))phenyl, 2-(2-(2-methylbutyl))phenyl, 3-(2-(2-methylbutyl))phenyl, 1-(3-(2-methylbutyl))phenyl, 2-(3-(2-methylbutyl))phenyl, 3-(3-(2-methylbutyl))phenyl, 1-(4-(2-methylbutyl))phenyl, 2-(4-(2-methylbutyl))phenyl, 3-(4-(2-methylbutyl))phenyl, 1-(1-(2,2-dimethylpropyl))phenyl, 2-(1-(2,2-dimethylpropyl))phenyl, 3-(1-(2,2-dimethylpropyl))phenyl, 1-(1-hexenyl)phenyl, 2-(1-hexenyl)phenyl, 3-(1-hexenyl)phenyl, 1-(2-hexenyl)phenyl, 2-(2-hexenyl)phenyl, 3-(2-hexenyl)phenyl, 1-(3-hexenyl)phenyl, 2-(3-hexenyl)phenyl, 3-(3-hexenyl)phenyl, 1-(1-(2-methylpentenyl))-phenyl, 2-(1-(2-methylpentenyl))phenyl, 3-(1-(2-methylpentenyl))phenyl, 1-(2-(2-methyl-pentenyl))phenyl, 2-(2-(2-methylpentenyl))phenyl, 3-(2-(2-methylpentenyl))phenyl, 1-(3-(2-methylpentenyl))phenyl, 2-(3-(2-methylpentenyl))phenyl, 3-(3-(2-methylpentenyl)) phenyl, 1-(4-(2-methylpentenyl))phenyl, 2-(4-(2-methylpentenyl))phenyl, 3-(4-(2-methyl-pentenyl))phenyl, 1-(5-(2-methylpentenyl))phenyl, 2-(5-(2-methylpentenyl))phenyl, 3-(5-(2-methylpentenyl))phenyl, 1-(1-(2,2-dimethylbutenyl))phenyl, 2-(1-(2,2-dimethyl-butenyl))phenyl, 3-(1-(2,2-dimethylbutenyl))phenyl, 1-(3-(2,2-dimethylbutenyl))phenyl, 2-(3-(2,2-dimethylbutenyl))phenyl, 3-(3-(2,2-dimethylbutenyl))phenyl, 1-(4-(2,2-dimethylbutenyl))phenyl, 2-(4-(2,2-dimethylbutenyl))phenyl, 3-(4-(2,2-dimethylbutenyl)) phenyl and the like.

In a preferred embodiment of the process according to the invention, compounds of the formula (I) are used in which Z in formula (I) is a group $CHR^3R^4$. Among these, preference is given to those compounds of the general formula (I) in which the variables $R^1$, $R^2$, $R^3$, $R^4$, independently of one another and in particular together have the following meanings:

$R^1$, $R^2$: are identical or different and are phenyl which is unsubstituted or carries 1, 2 or 3 substituents which are selected from methyl and methoxy, where $R^1$ and $R^2$ are in each case in particular unsubstituted phenyl;

$R^3$ is $C_1$- to $C_4$-alkyl, in particular methyl;

$R^4$ is $C_1$- to $C_4$-alkyl which is unsubstituted or carries a group $P(=O)R^{4a}R^{4b}$, where $R^4$ is in particular methyl or ethyl or is a group $CH_2$—$P(=O)R^{4a}R^{4b}$ or $CH(CH_3)$—$P(=O)R^{4a}R^{4b}$;

or $R^3$, $R^4$: together with the carbon atom to which they are bonded, is $C_3$- to $C_8$-cycloalkyl in which one or two $CH_2$ groups can be replaced by one or two nonadjacent oxygen atoms and where $C_3$- to $C_6$-cycloalkyl is unsubstituted or carries a group A-$P(=O)R^{4a}R^{4b}$ and/or has 1, 2, 3 or 4 methyl groups as substituents, where $R^3$ and $R^4$, together with the carbon atom to which they are bonded, are in particular cyclopentyl, oxolan-3-yl, 2,2-dimethyl-1,3-dioxolan-4-yl or cyclohexyl, or $R^3$ and $R^4$, together with the carbon atom to which they are bonded, can be bicyclo[2.2.1]heptan-1-yl that has a group $P(=O)R^{4a}R^{4b}$ in the 2 position;

where

A is a chemical bond, $CH_2$ or $CH(CH_3)$; and $R^{4a}$, $R^{4b}$: are identical or different and are $C_6$- to $C_{10}$-aryl and in particular phenyl which is unsubstituted or carries 1, 2 or 3 substituents which are selected from methyl and methoxy, where $R^{4a}$ and $R^{4b}$ are in particular phenyl which is unsubstituted or carries 1, 2 or 3 substituents which are selected from methyl and methoxy, where particularly preferably $R^{4a}$ and $R^{4b}$ are in each case unsubstituted phenyl.

In a particularly preferred embodiment of the process according to the invention, compounds of the formula (I) are used in which Z in formula (I) is a group $CHR^3R^4$ and in which the variables $R^1$, $R^2$, $R^3$, $R^4$, independently of one another and particularly together have the following meanings:

$R^1$, $R^2$: are identical or different and are phenyl which is unsubstituted or carries 1, 2 or 3 substituents which are selected from methyl and methoxy, where $R^1$ and $R^2$ are in each case in particular unsubstituted phenyl;

$R^3$ is $C_1$- to $C_4$-alkyl, in particular methyl;

$R^4$ is $C_1$- to $C_4$-alkyl which carries a group $P(=O)R^{4a}R^{4b}$, where and in particular one group is $CH_2$—$P(=O)R^{4a}R^{4b}$ or $CH(CH_3)$—$P(=O)R^{4a}R^{4b}$ where $R^{4a}$, $R^{4b}$: are identical or different and are phenyl which is unsubstituted or carries 1, 2 or 3 substituents which are selected from methyl and methoxy, where particularly preferably $R^{4a}$ and $R^{4b}$ are in each case unsubstituted phenyl.

In this particularly preferred embodiment of the process according to the invention, in particular a compound of the formula (I) is used in which $R^1$, $R^2$: are unsubstituted phenyl;

$R^3$ is methyl;

$R^4$ is a group $CH(CH_3)$—$P(=O)R^{4a}R^{4b}$, in which $R^{4a}$ and $R^{4b}$ are in each case unsubstituted phenyl.

Here, the compound is (2-(diphenylphosphoryl)-1-methylpropyl))diphenylphosphane, including its (R,R)-enantiomers (=(R,R)-chiraphos monoxide) and its (S,S)-enantiomers (=(S,S)-chiraphos monoxide), as well as its racemate (compounds (I-1)).

If the radicals $R^3$ and $R^4$ in the general formula (I) have a different meaning or, together with the carbon atom to which they are bonded, are a bicyclic and/or substituted cycloalkyl radical, the carbon atom which carries the radicals $R^3$ and $R^4$ can have a (R) or (S) configuration. These compounds of the general formula (I) can be present as pure (R) or pure (S) stereoisomers or as mixtures thereof. As a rule, in these cases the pure (R) and (S) stereoisomers will be used, with any stereoisomer mixtures also being suitable for use in the present process.

Here and in what follows, a pure stereoisomer is understood as meaning chiral substances which, with regard to the desired stereoisomer, have an enantiomer excess (ee) of at least 80% ee, in particular at least 90% ee and specifically at least 95% ee.

In another embodiment of the process according to the invention, compounds of the formula (I) are used in which Z in formula (I) is aryl which is unsubstituted or carries one or more, e.g. 1, 2, 3, 4 or 5, substituents which are selected from $C_1$- to $C_6$-alkyl, $C_3$- to $C_6$-cycloalkyl, $C_5$- to $C_{10}$-aryl, $C_1$- to $C_6$-alkoxy and amino. Among these, preference is given to those compounds of the general formula (I) in which the variables $R^1$, $R^2$, Z, independently of one another and in particular together, have the following meanings:

Z is phenyl which is unsubstituted or carries 1, 2 or 3 substituents which are selected from methyl and methoxy;

$R^1$, $R^2$: are identical or different and are phenyl which is unsubstituted or carries 1, 2 or 3 substituents which are selected from methyl and methoxy, where $R^1$ and $R^2$ are in each case in particular unsubstituted phenyl.

Particularly preferred compounds of the general formula (I) are, for example:
- (2-(diphenylphosphoryl)-1-methylpropyl))diphenylphosphane, including its (R,R)-enantiomer (=(R,R)-chiraphos monoxide) and its (S,S)-enantiomer (=(S,S)-chiraphos monoxide), and its racemate (compounds (I-1)),
- cyclopentyldiphenylphosphine (compound (I-2),
- 2-butyldiphenylphosphine (compound (I-3),
- cyclohexyldiphenylphosphine (compound (I-4),
- isopropyldiphenylphosphine (compound (I-5),
- [5-(diphenylphosphanylmethyl)-2,2-dimethyl-1,3-dioxolan-4-yl]methyldiphenyl-phosphane monoxide, including its (4S,5S) and (4R,5R) enantiomers and its racemate (compounds (I-6),
- [5-(1-diphenylphosphanylethyl)-2,2-dimethyl-1,3-dioxolan-4-yl]ethyldiphenyl-phosphane monoxide, including its (4S,5S) and (4R,5R) enantiomers and its racemate (compounds (I-7),
- [2-diphenylphosphanylcyclohexyl]diphenylphosphane monoxide, including its (1S,2S) and (1R,2R) enantiomers and its racemate (compounds (I-8),
- [4-diphenylphosphanyltetrahydrofuran-3-yl]diphenylphosphane monoxide, including its (3S,4S) and (3R,4R) enantiomers and its racemate (compounds (I-9),
- [2-diphenylphosphanyl-3-bicyclo[2.2.1]hept-5-enyl]diphenylphosphane monoxide, including its (1S,2R,3R,4R), (1R,2S,3R,4R), (1S,2R,3S,4S), (1R,2S,3S,4S) isomers, and enantiomer and diastereomer mixtures thereof (compounds (I-10),
- [1-benzyl-4-diphenylphosphanylpyrrolidin-3-yl]diphenylphosphane monoxide, including its (3S,4S) and (3R,4R) enantiomers and its racemate (compounds (I-11),
- [3-diphenylphosphanyl-1-methylbutyl]diphenylphosphane monoxide, including its (1S,3S) and (1R,3R) enantiomers and its racemate (compounds (I-12), and mixtures thereof.

Likewise of suitability is triphenylphosphine (compound (I-13)) and its mixtures with one or more of the aforementioned compounds of the formula (I), e.g. with one of the compounds (I-1) to (I-12).

The compound of the formula (I) is used in the process according to the invention usually in an amount of from 0.01 to 1 mol, preferably 0.02 to 0.8 mol, particularly preferably 0.03 to 0.7 mol and in particular in an amount of from 0.05 to 0.6 mol per mole of rhodium.

Suitable feed materials in the process according to the invention are generally all types of prochiral carbonyl compounds which have a double bond at the 2 position. Preferably, the prochiral α,β-unsaturated carbonyl compound is prochiral, α,β-unsaturated ketone or in particular prochiral, α,β-unsaturated aldehydes.

Accordingly, the process according to the invention is preferably suitable for the preparation of optically active aldehydes or ketones by asymmetric hydrogenation of prochiral α,β-unsaturated aldehydes or ketones. The process according to the invention is particularly preferably suitable for the preparation of optically active aldehydes by asymmetric hydrogenation of prochiral α,β-unsaturated aldehydes.

In a preferred embodiment of the process according to the invention, the prochiral α,β-unsaturated carbonyl compound is selected from compounds of the general formula (II)

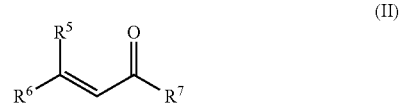

in which
$R^5$, $R^6$ are different from one another and is in each case an unbranched, branched or cyclic hydrocarbon radical having 1 to 25 carbon atoms which is saturated or has one or more, e.g. 1, 2, 3, 4 or 5, preferably nonconjugated ethylenic double bonds, and which is unsubstituted or carries one or more, e.g. 1, 2, 3 or 4, identical or different substituents which are selected from $OR^8$, $NR^{9a}R^{9b}$, halogen, $C_6$- to $C_{10}$-aryl and $C_3$- to $C_9$-hetaryl;

$R^7$ is hydrogen or an unbranched, branched or cyclic hydrocarbon radical having 1 to 25 carbon atoms which is saturated or has one or more, e.g. 1, 2, 3, 4 or 5, preferably nonconjugated ethylenic double bonds, and which is unsubstituted or carries one or more, e.g. 1, 2, 3 or 4, identical or different substituents which are selected from $OR^8$, $NR^{9a}R^{9b}$, halogen, $C_6$- to $C_{10}$-aryl and $C_3$- to $C_9$-hetaryl;

or $R^7$ together with one of the radicals $R^5$ or $R^6$, can also be a 3- to 25-membered alkylene group, in which 1, 2, 3 or 4 nonadjacent $CH_2$ groups can be replaced by O or N—$R^{9c}$, where the alkylene group is saturated or has one or more, e.g. 1, 2, 3, 4 or 5, preferably nonconjugated ethylenic double bonds, and where the alkylene group is unsubstituted or carries or one or more, e.g. 1, 2, 3 or 4, identical or different substituents which are selected from $OR^8$, $NR^{9a}R^{9b}$, halogen, $C_1$- to $C_4$-alkyl, $C_6$- to $C_{10}$-aryl and $C_3$- to $C_9$-hetaryl, where two substituents also together can be a 2- to 10-membered alkylene group, where the 2- to 10-membered alkylene group is saturated or has one or more, e.g. 1, 2, 3 or 4, nonconjugated ethylenic double bonds, and where the 2- to 10-membered alkylene group is unsubstituted or carries one or more, e.g. 1, 2, 3 or 4, identical or different substituents which are selected from $OR^8$, $NR^{9a}R^{9b}$, halogen, $C_6$- to $C_{10}$-aryl and $C_3$- to $C_9$-hetaryl;

where $R^8$ is hydrogen, $C_1$- to $C_6$-alkyl, $C_6$- to $C_{10}$-aryl, $C_7$- to $C_{12}$-aralkyl or $C_7$- to $C_{12}$-alkylaryl;

$R^{9a}$, $R^{9b}$ in each case independently of one another are hydrogen, $C_1$- to $C_6$-alkyl, $C_6$- to $C_{10}$-aryl, $C_7$- to $C_{12}$-aralkyl or $C_7$- to $C_{12}$-alkylaryl or $R^{9a}$ and $R^{9b}$ together can also be an alkylene chain having 2 to 5 carbon atoms, which can be interrupted by N or O; and $R^{9c}$ is hydrogen, $C_1$- to $C_6$-alkyl, $C_6$- to $C_{10}$-aryl, $C_7$- to $C_{12}$-aralkyl or $C_7$- to $C_{12}$-alkylaryl.

The unbranched, branched or cyclic hydrocarbon radicals having 1 to 25 carbon atoms specified in the definition of radicals $R^5$, $R^6$ and $R^7$ are usually unbranched $C_1$- to $C_{25}$-alkyl groups, unbranched $C_2$- to $C_{25}$-alkenyl groups, unbranched $C_4$- to $C_{25}$-alkadienyl groups, branched $C_3$- to $C_{25}$-alkyl groups, branched $C_3$- to $C_{25}$-alkenyl groups, branched $C_5$- to $C_{25}$-alkadienyl groups, and also $C_3$- to $C_{25}$-cycloalkyl groups or $C_3$- to $C_{24}$-cycloalkyl groups which are substituted by one or more, e.g. by 1, 2, 3 or 4, $C_1$- to $C_4$-alkyl groups, as defined above. The cyclic hydrocarbon radicals also include both cyclic hydrocarbon radicals which have a phenyl ring which optionally carries one or more, e.g. 1, 2, 3, 4, 5 or 6, $C_1$-$C_4$-alkyl groups, where the phenyl ring is bonded directly to the ethylenically unsaturated double bond or the carbonyl group in formula (II) or is bonded via a $C_1$-$C_6$-alkylene group.

An alkenyl group is understood as meaning a linear or branched aliphatic hydrocarbon radical which is monounsaturated. An alkdienyl group is understood as meaning a linear or branched aliphatic hydrocarbon radical which is diunsaturated. The 3- to 25-membered alkylene groups specified in the definition of the radical $R^7$ that are saturated are generally unbranched or branched $C_3$- to $C_{25}$-alkylene groups, as defined above.

The 3- to 25-membered alkylene groups which have one or more, e.g. 1, 2, 3 or 4, nonconjugated ethylenic double bonds specified in the definition of the radical $R^7$ are generally unbranched or branched $C_3$- to $C_{25}$-alkenylene groups, as defined above.

Preferably, one of the radicals $R^5$, $R^6$ is methyl or ethyl, in particular methyl, and the other radical is an unbranched, branched or cyclic hydrocarbon radical having 3 to 25 carbon atoms which is saturated or has one or more. e.g. 1, 2, 3, 4 or 5, preferably nonconjugated ethylenic double bonds, and which is unsubstituted or carries one or more, e.g. 1, 2, 3 or 4, identical or different substituents which are selected from $OR^8$, $NR^{9a}R^{9b}$, halogen, $C_6$- to $C_{10}$-aryl and $C_3$- to $C_9$-hetaryl.

In particular, one of the radicals $R^5$, $R^6$ is methyl or ethyl, in particular methyl, and the other radical is an unbranched, branched or cyclic hydrocarbon radical having 3 to 25 carbon atoms which is saturated or has one or more, e.g. 1, 2 or 3, preferably nonconjugated ethylenic double bonds.

$R^7$ is in particular hydrogen.

In a very preferred embodiment of the process according to the invention, the prochiral α,β-unsaturated carbonyl compound is selected from compounds of the general formula (IIa) and (IIb)

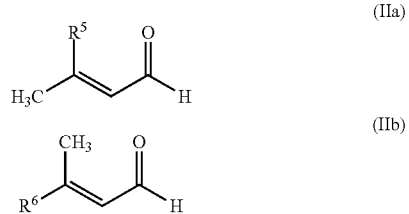

(IIa)

(IIb)

in which
$R^5$, $R^6$ is in each case an unbranched or branched hydrocarbon radical having 2 to 25, in particular having 3 to 20, carbon atoms which is saturated or has 1, 2, 3, 4 or 5 nonconjugated ethylenic double bonds.

Accordingly, the process according to the invention can be used, by way of asymmetric hydrogenation of prochiral α,β-unsaturated aldehydes or ketones of the general formulae (II), (IIa) and (IIb), to prepare the corresponding α,β-saturated aldehydes or ketones of the formula (III) in optically active form, where the carbon atom which carries the radicals $R^5$ and $R^6$ constitutes the asymmetry center generated by the hydrogenation.

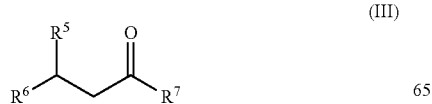

(III)

In formula (III), $R^5$, $R^6$ and $R^7$ have the meanings specified for formula (II), in particular those specified for the formulae (IIa) and (IIb).

The asymmetric, i.e. enantioselective hydrogenation according to the invention of the α,β-unsaturated aldehydes of the formulae (IIa) or (IIb) renders accessible the corresponding α,β-saturated aldehydes. The compounds of the formulae (IIa) and (IIb) constitute E/Z double-bond isomers relative to one another. In principle, the correspondingly optically active aldehydes are accessible starting from both double-bond isomers of the formulae (IIa) and (IIb). Depending on the choice of the enantiomeric form of the catalyst, i.e. depending on the choice of the (+) or (−) enantiomer of the catalyst or of the (+) or (−) enantiomer of the chiral ligand used, preferably one of the enantiomers of the optically active aldehyde is obtained in a manner according to the invention from the E or Z double-bond isomer used. The same is true for the aforementioned substrate and product classes. In principle, it is also possible to react mixtures of the two double-bond isomers in a manner according to the invention. This gives mixtures of the two enantiomers of the desired target compound.

Examples of optically active aldehydes or ketones which can be prepared using the process according to the invention include the following compounds:

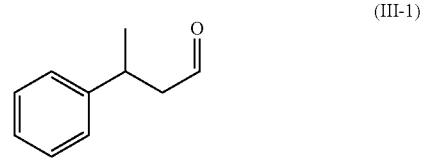

(III-1)

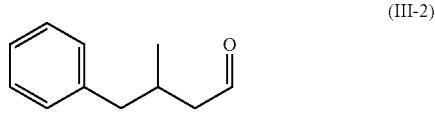

(III-2)

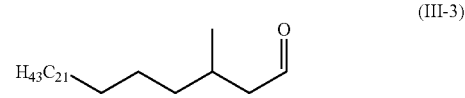

(III-3)

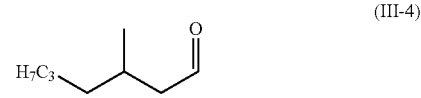

(III-4)

(III-5)

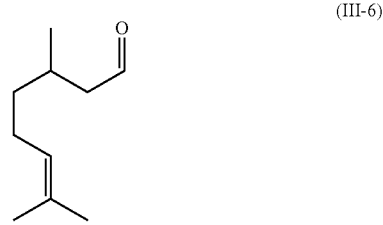

(III-6)

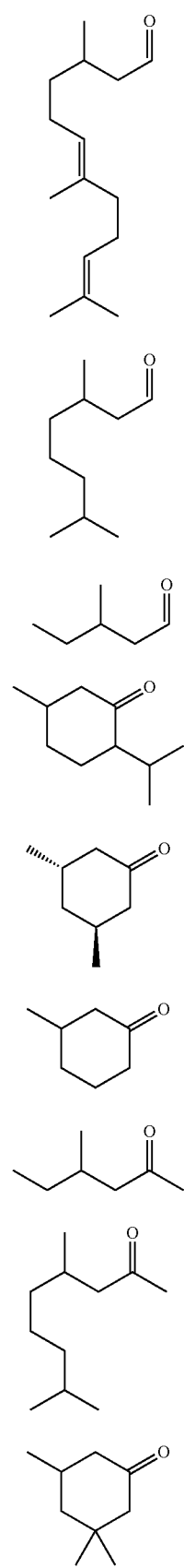
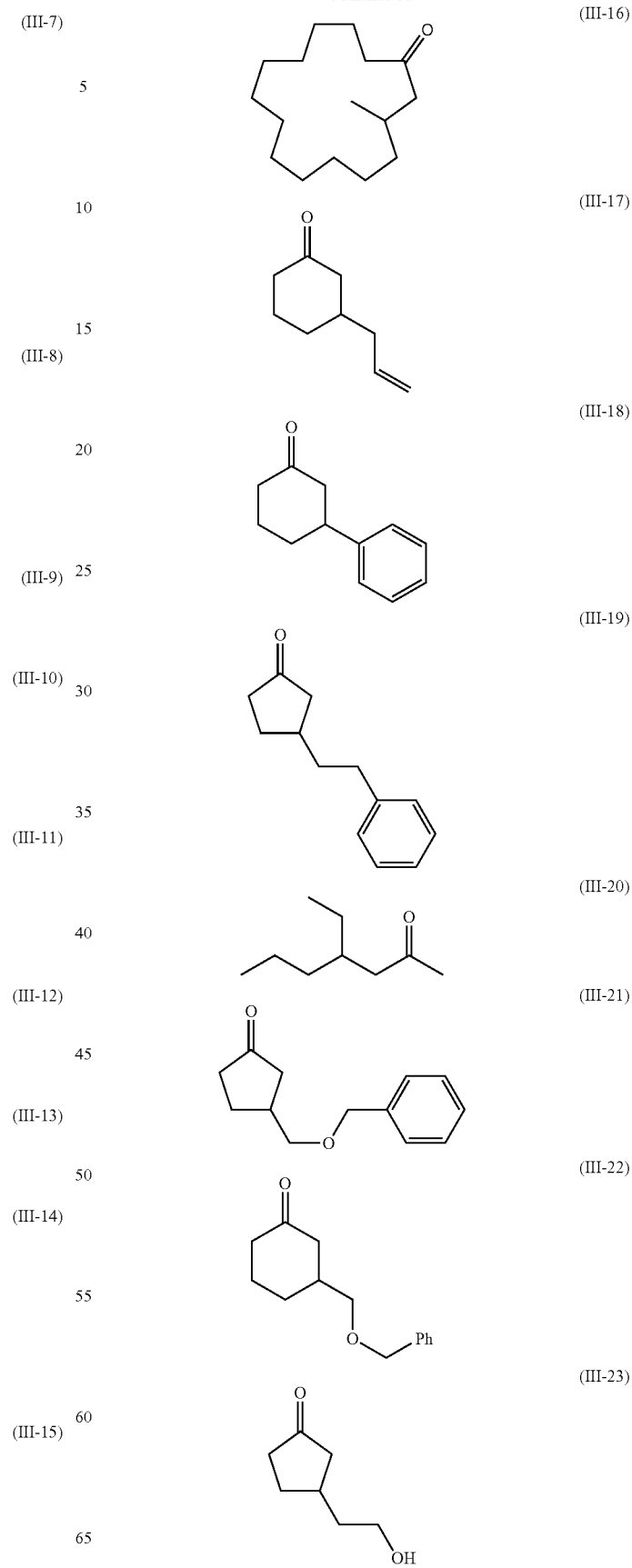

-continued

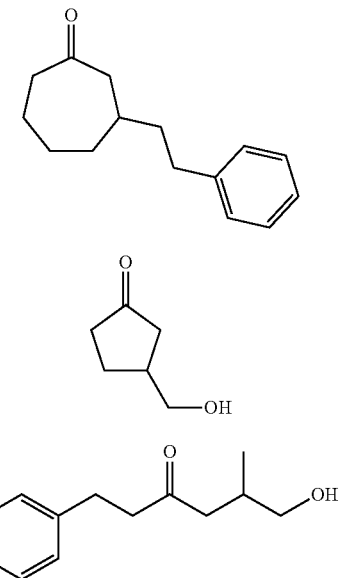

(III-24)

(III-25)

(III-26)

The process according to the invention is particularly preferably suitable for the preparation of optically active citronellal of the formula (IV)

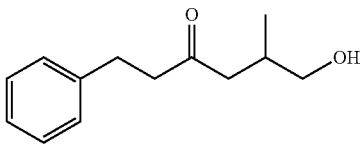

(IV)

in which * denotes the asymmetry center; by asymmetric hydrogenation of geranial of the formula (IIa-1) or of neral of the formula (IIb-1)

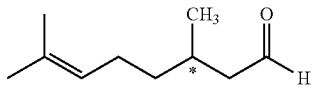

(IIa-1)

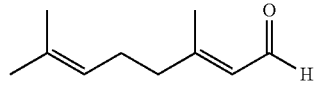

(IIb-1)

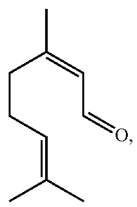

Mixtures of geranial and neral can also be reacted in the manner according to the invention, wherein, as described above, mixtures of D- or L-citronellal are obtained which are optically active if the two enantiomers are not present therein in equal parts.

Of particular preference in the context of the process according to the invention is the preparation according to the invention of D-citronellal by asymmetric hydrogenation of neral or geranial.

The preparation process according to the invention is carried out in the presence of an optically active transition metal catalyst that is soluble in the reaction mixture and which comprises rhodium as catalytically active transition metal.

Catalysts of this type are obtainable for example by reaction of at least one suitable rhodium compound soluble in the reaction mixture with an optically active ligand which has at least one phosphorus and/or arsenic atom.

Suitable rhodium compounds are in particular those which are soluble in the selected reaction medium, such as, for example, rhodium (0), rhodium(I), rhodium(II) and rhodium(III) salts such as e.g. rhodium(III) chloride, rhodium (III) bromide, rhodium(III) nitrate, rhodium(III) sulfate, rhodium(II) or rhodium(III) oxide, rhodium(II) or rhodium (III) acetate, rhodium(II) or rhodium(III) carboxylate, $Rh(acac)_3$, $[Rh(cod)Cl]_2$, $[Rh(cod)_2]BF_4$, $Rh_2(OAc)_4$, bis (ethylene)rhodium(I)acac, $Rh(CO)_2acac$, $[Rh(cod)OH]_2$, $[Rh(cod)OMe]_2$, $Rh_4(CO)_{12}$ or $Rh_6(CO)_{16}$, where "acac" is an acetylacetonate ligand, "cod" is a cyclooctadiene ligand and "OAc" is an acetate ligand.

Preferably, the rhodium compound used is $Rh(OAc)_3$, $[Rh(cod)Cl]_2$, $Rh(CO)_2$ acetylacetonate, $[Rh(cod)OH]_2$, $[Rh(cod)OMe]_2$, $Rh_4(CO)_{12}$ or $Rh_6(CO)_{16}$, $Rh_2(OAc)_4$ and bis (ethylene)rhodium(I) acetylacetonate. In particular, the rhodium compound used is $Rh(CO)_2acac$, $Rh_2(OAc)_4$ and bis (ethylene)rhodium(I) acetylacetonate.

The specified and further suitable rhodium compounds or rhodium complexes are known and adequately described in the literature or can be prepared by the person skilled in the art analogously to the compounds already known.

The specified rhodium compounds or rhodium complexes are used according to the invention usually in an amount of about 0.001 to about 1 mol %, preferably from about 0.002 to about 0.5 mol %, in particular from about 0.005 to about 0.2 mol % (based on the transition metal atoms present) in the ratio to the amount of substrate to be hydrogenated.

In the case of reactions carried out under continuous conditions, the ratio of amount of transition metal compound used as precursor of the homogeneous catalyst according to the invention to the amount of substrate to be hydrogenated is advantageously chosen such that a catalyst concentration in the range from about 100 ppm to 10 000 ppm, in particular in the range from about 200 ppm to 5000 ppm, is observed.

According to the invention, the specified rhodium compounds and rhodium complexes are brought into contact with a further compound which is optically active, preferably essentially enantiomerically pure (i.e. has an enantiomer excess of at least 90% ee, in particular at least 95% ee or at least 98% ee or at least 99% ee) and has two phosphorus atoms. This compound, to be referred to as chiral ligand, forms the transition metal catalyst to be used according to the invention with the transition metal compound used in the reaction mixture or in a preformation stage upstream of the hydrogenation.

According to the invention, those chiral ligands are used which have two phosphorus atoms and form chelate complexes with the transition metal used and which are referred to hereinbelow as bidentate bisphosphine ligands.

Suitable chiral bidentate bisphosphine ligands in the context of the present invention are those compounds which are described for example in: I. Ojima (ed.), *Catalytic Asymmetric Synthesis*, Wiley-VCh, 2nd edition, 2000 or in E. N. Jacobsen, A. Pfaltz, H. Yamamoto (ed.), *Comprehensive Asymmetric Catalysis*, 2000, Springer or in W. Tang, X. Zhang, *Chem. Rev.* 2003, 103, 3029-3069.

By way of example, the following compounds may be listed as chiral ligands (1) to (90) to be used with preference according to the invention, as well as their enantiomers:

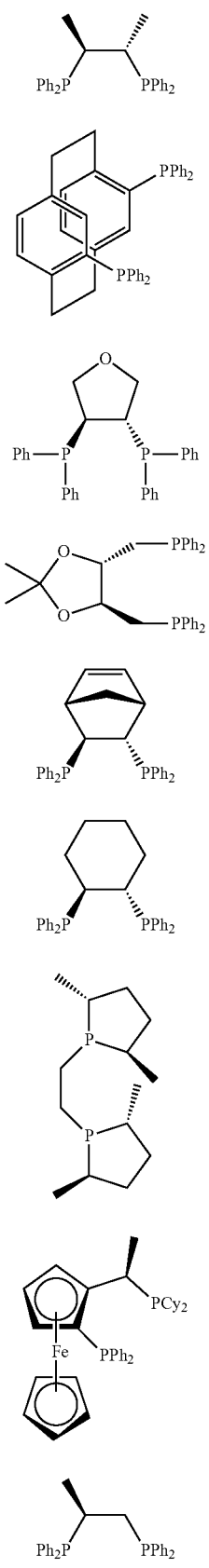

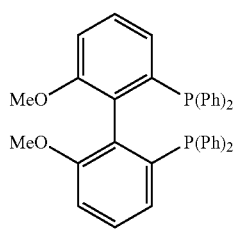
(17)
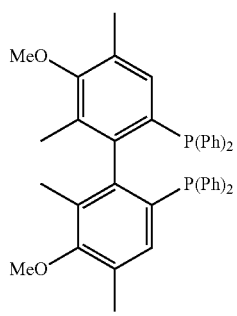
(18)
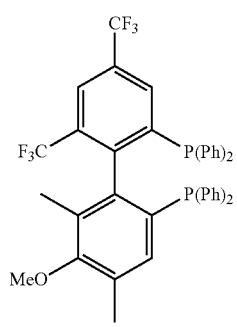
(19)
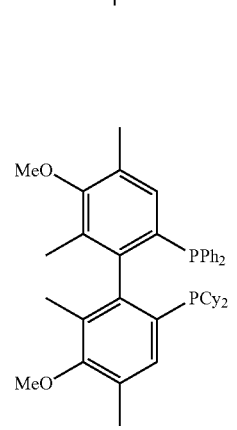
(20)
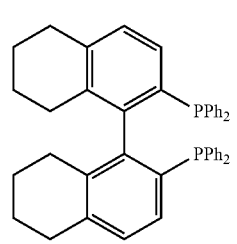
(21)
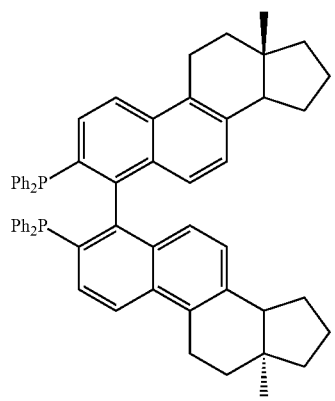
(22)
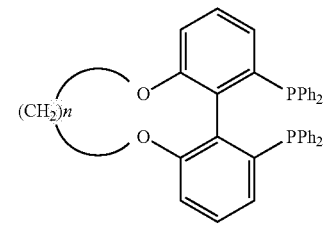
(23)
n = 1-6
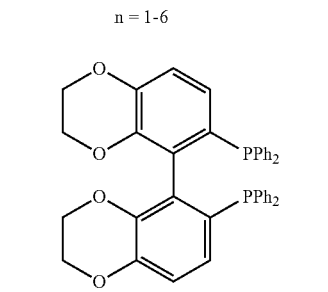
(24)
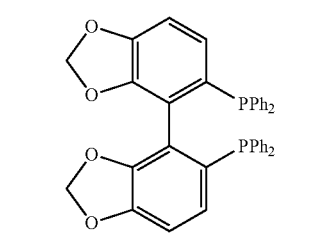
(25)
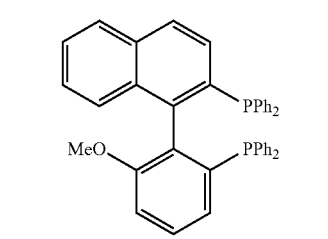
(26)
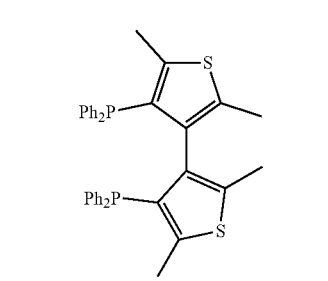
(27)

-continued
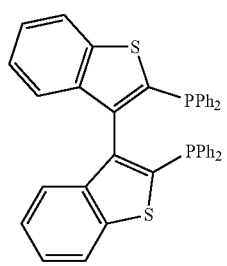
(28)
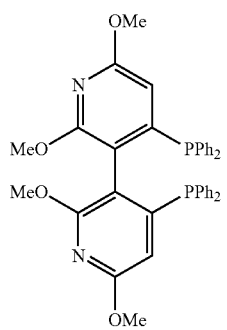
(29)
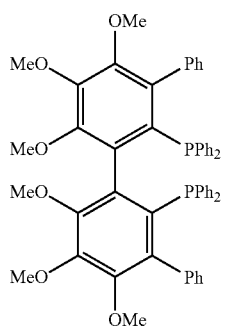
(30)
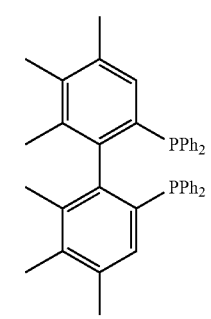
(31)
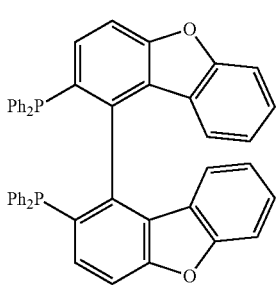
(32)
-continued
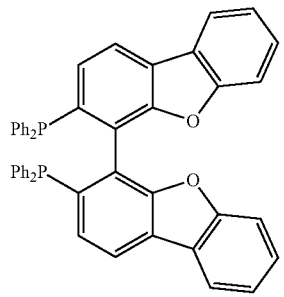
(33)
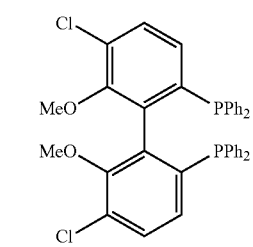
(34)
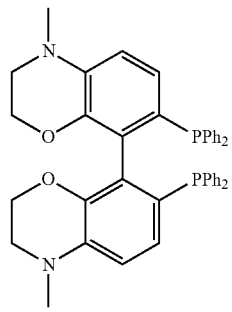
(35)
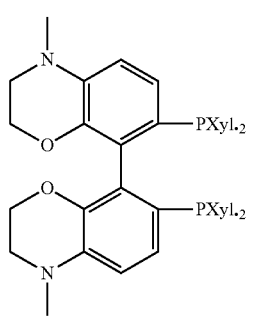
(36)
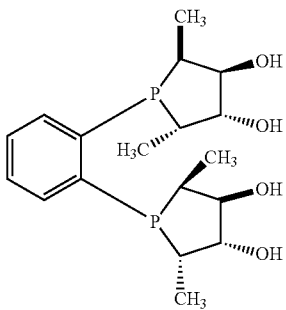
(37)

(38)
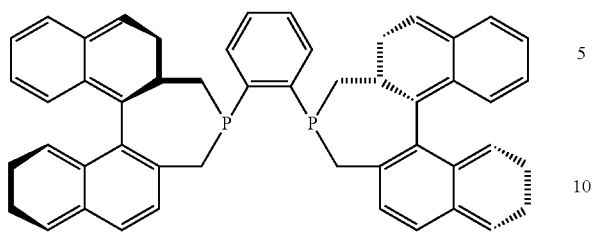
(39)
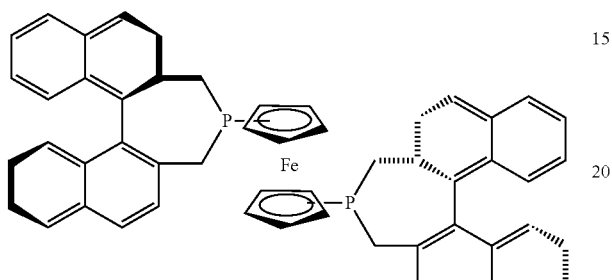
(40)
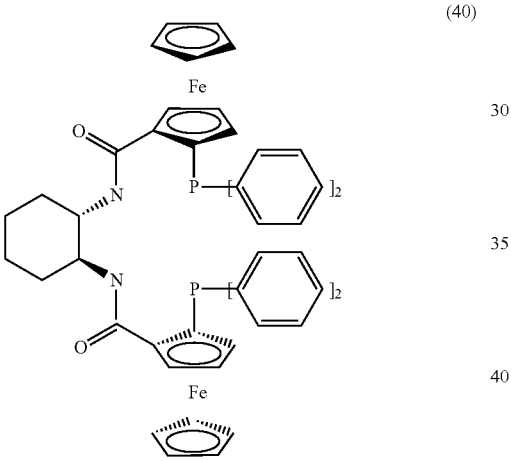
(41)
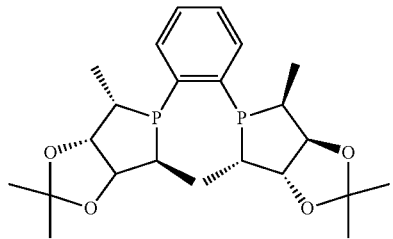
(42)
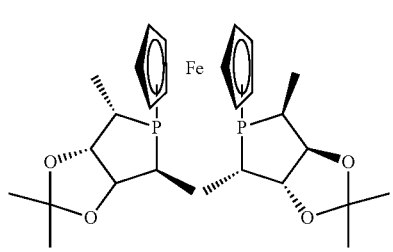
(43)
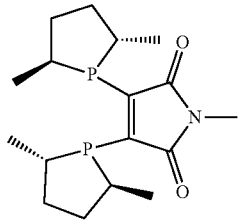
(44)
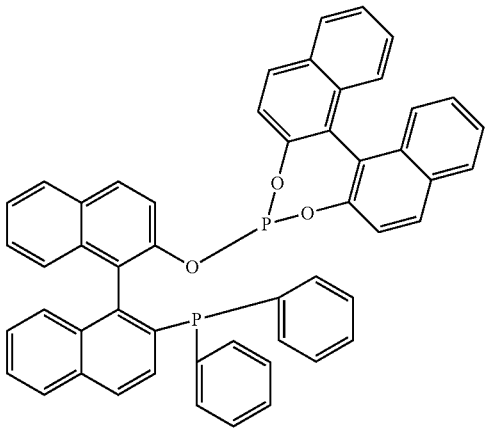
(45)
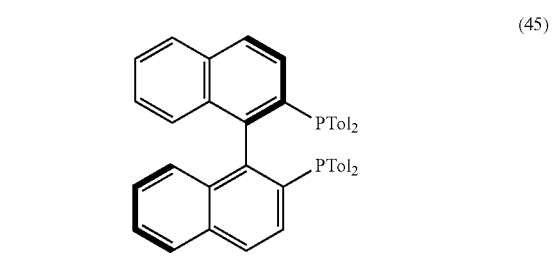
(46)
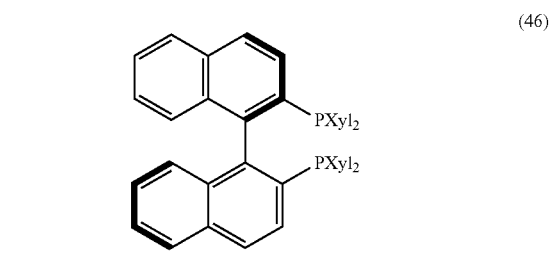
(47)
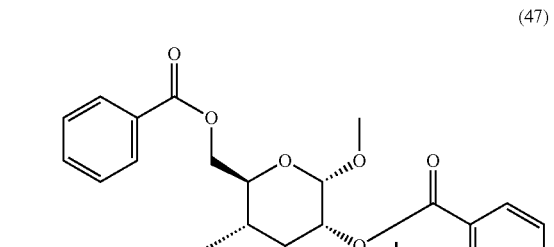

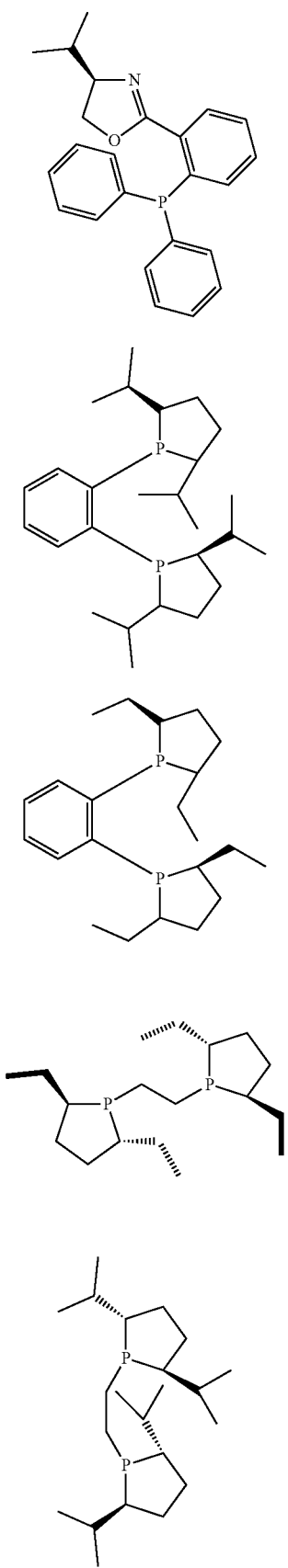
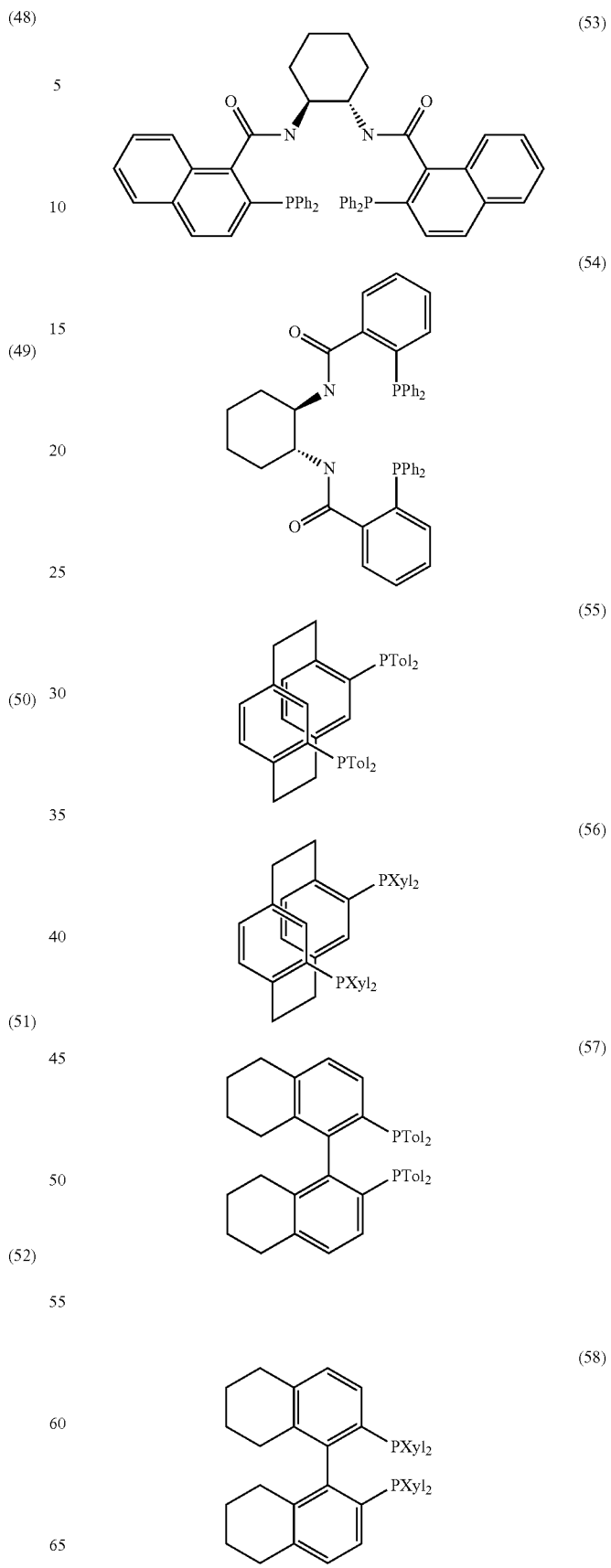

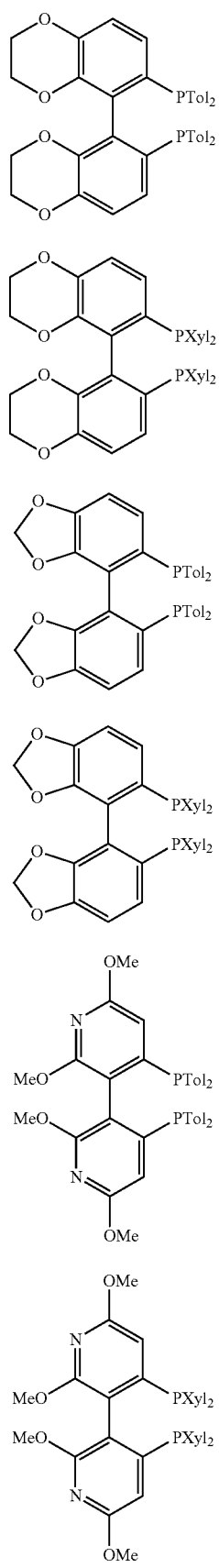
(59)
(60)
(61)
(62)
(63)
(64)
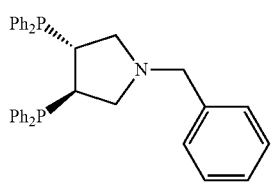
(65)
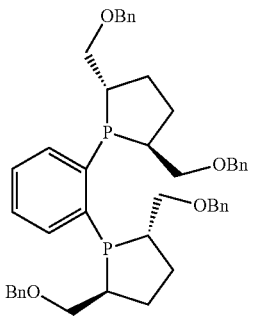
(66)
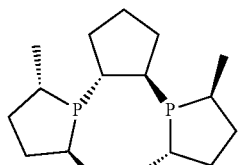
(67)
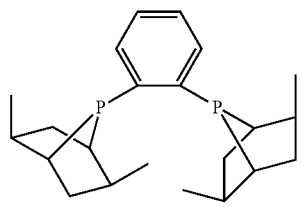
(68)
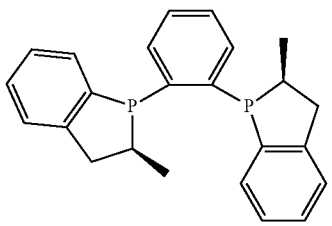
(69)
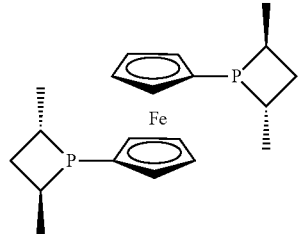
(70)
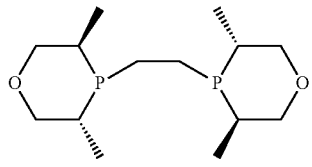
(71)

(72)
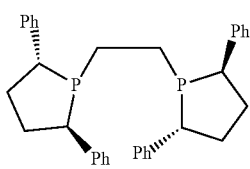
(73)
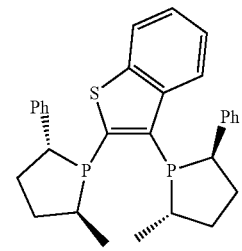
(74)
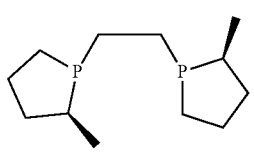
(75)
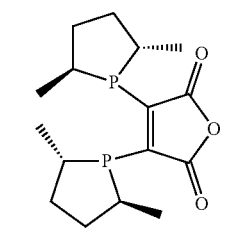
(76)
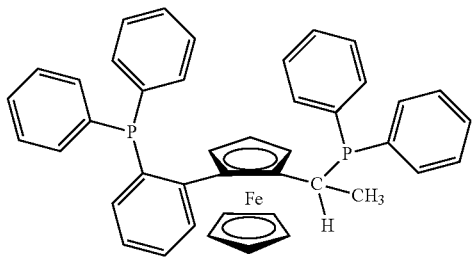
(77)
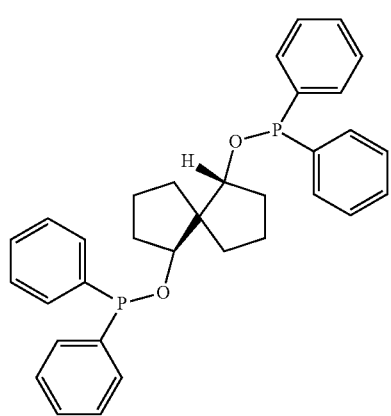
(78)
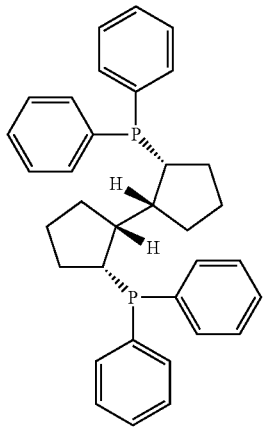
(79)
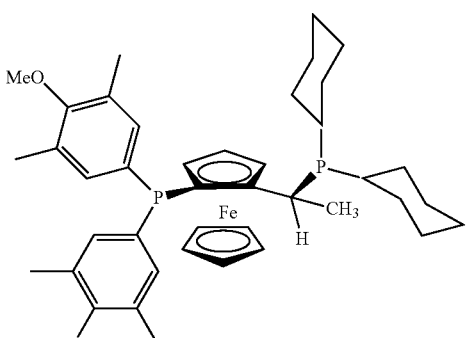
(80)
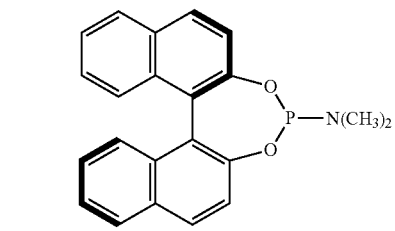
(81)
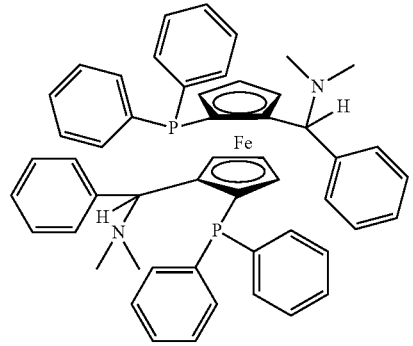
(82)

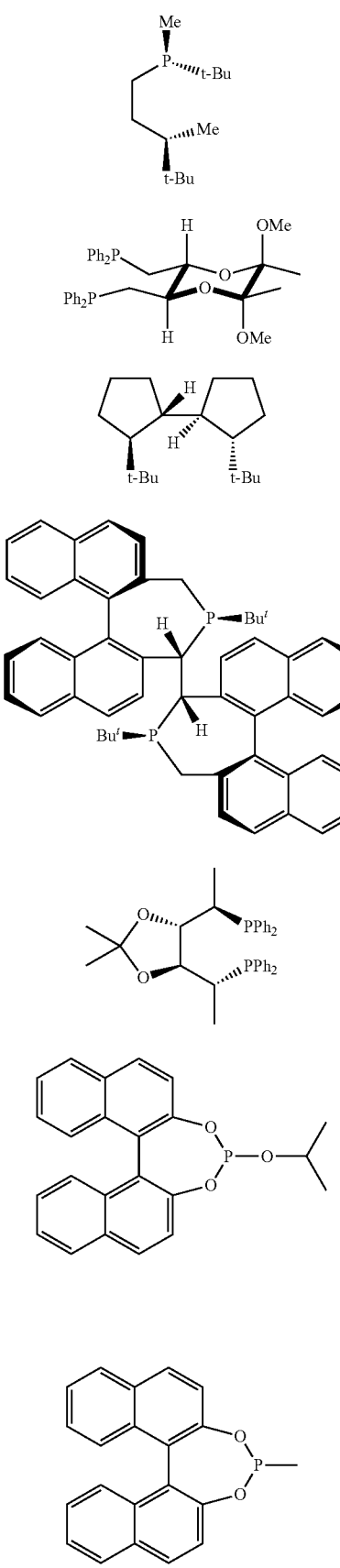

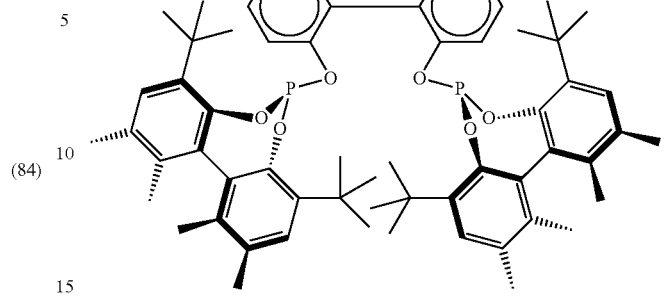

In the formulae (1) to (90), "Ph" is to be understood as meaning phenyl, "Cy" cyclohexyl, "Xyl" xylyl, "Tol" p-tolyl and "Bn" benzyl.

Ligands that are particularly preferred according to the invention are those of the structural formulae (1) to (14) and also (37), (38), (41), (43), (49), (50), (51), (52), (65), (66), (67), (68), (69), (71), (72), (73), (74), (75), (83), (84), (85), (86), (87).

Particularly preferred chiral, bidentate bisphosphine ligands are those of the general formulae (IX), (X) or (XI)

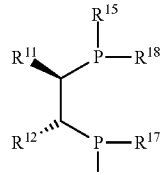

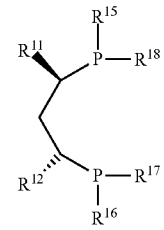

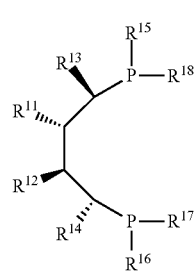

in which $R^{11}$, $R^{12}$: in each case independently of one another are an unbranched, branched or cyclic hydrocarbon radical having 1 to 20 carbon atoms which is saturated or can have one or more, generally 1 to about 4, nonconjugated, ethylenic double bonds and is unsubstituted or carries one or more, generally 1 to 4, identical or different substituents which are selected from $OR^{19}$, $NR^{20}R^{21}$, halogen, $C_6$-$C_{10}$-aryl and $C_3$-$C_9$-hetaryl, or $R^{11}$ and $R^{12}$ together can also be a 2 to 10-membered alkylene group or a 3- to 10-membered cycloalkylene group, in which 1, 2, 3 or 4 nonadjacent $CH_2$ groups can be replaced by O or N—$R^{9c}$, where the alkylene group and the cycloalkylene group are saturated or have one or two nonconjugated ethylenic double bonds, and where the alkylene group and the cycloalkylene group are unsubstituted or carry one or more identical or different substituents which are selected from $C_1$- to $C_4$-alkyl;

$R^{13}$, $R^{14}$: are in each case independently of one another hydrogen or straight-chain or branched $C_1$- to $C_4$-alkyl and $R^{15}$, $R^{16}$, $R^{17}$, $R^{18}$: are identical or different and are $C_6$- to $C_{10}$-aryl which is unsubstituted or carries one or more substituents which are selected from $C_1$- to $C_6$-alkyl, $C_3$- to $C_6$-cycloalkyl, $C_6$- to $C_{10}$-aryl, $C_1$- to $C_6$-alkoxy and amino;

$R^{19}$, $R^{20}$, $R^{21}$: are in each case independently of one another hydrogen, $C_1$-$C_4$-alkyl, $C_6$-$C_{10}$-aryl, $C_7$-$C_{12}$-aralkyl or $C_7$-$C_{12}$-alkylaryl, where $R^{20}$, $R^{21}$: can together also be an alkylene chain having 2 to 5 carbon atoms, which can be interrupted by N or O.

With regard to the formulae (IX), (X) and (XI), the variables have in particular the following meaning:

$R^{11}$, $R^{12}$: are in each case independently of one another an unbranched, branched or $C_1$- to $C_4$-alkyl radical or $R^{11}$ and $R^{12}$ are together or are a $C_3$- to $C_7$-alkanediyl radical, $C_3$- to $C_7$-alkenediyl radical, $C_5$- to $C_7$-cycloalkanediyl radical or a $C_5$- to $C_7$-cycloalkenediyl radical, where the four aforementioned radicals are unsubstituted or carry one or more identical or different substituents selected from $C_1$- to $C_4$-alkyl;

$R^{13}$, $R^{14}$: in each case independently of one another are hydrogen or straight-chain or branched $C_1$- to $C_4$-alkyl and $R^{15}$, $R^{16}$, $R^{17}$, $R^{18}$: are phenyl.

Chiral, bidentate bisphosphine ligands particularly preferred in the context of the process according to the invention are those of the general formula (IX), in particular the compounds of the formula (1) referred to hereinbelow as "chiraphos" or of the formulae (IXa) or (IXb),

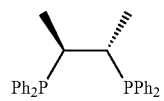

(IXa)

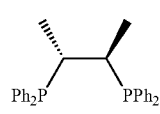

(IXb)

Also of suitability are the compound of the formula (5) referred to as "Norphos" and/or of the formulae (IXc) or (IXd),

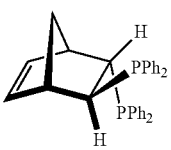

(IXc)

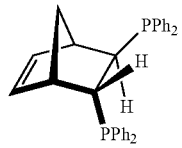

(IXd)

In the formulae (IXa) to (IXd) Ph is phenyl.

According to the invention, the selected chiral ligands are used in each case in the form of their two enantiomers. The chiral ligands typically have an enantiomer excess (ee) of at least 80% ee, in particular at least 90% ee and specifically at least 95% ee.

When using chiral ligands with two phosphorus atoms, these are advantageously used in an amount of about 0.9 to about 10 mol, preferably about 1 to about 4 mol per mole of transition metal compound used.

Preferably, the optically active rhodium catalyst soluble in the reaction mixture is generated in-situ before or during the hydrogenation by reaction of an achiral rhodium compound and with a chiral, bidentate bisphosphine ligand.

In this connection, the expression "in situ" means that the catalyst is generated directly before or at the start of the hydrogenation. Preferably, the catalyst is generated before the hydrogenation.

In a preferred embodiment of the process according to the invention, the catalyst is pretreated before the hydrogenation with a gas mixture comprising carbon monoxide and hydrogen, and/or the asymmetric hydrogenation is carried out in the presence of carbon monoxide additionally introduced to the reaction mixture.

This means that the rhodium catalyst used, which is soluble in the reaction mixture, i.e. homogeneous, is either pretreated before the asymmetric hydrogenation with a gas mixture which comprises carbon monoxide and hydrogen (i.e. a so-called preformation is carried out) or the asymmetric hydrogenation is carried out in the presence of carbon monoxide additionally introduced into the reaction mixture or a preformation is carried out and then the asymmetric hydrogenation is carried out in the presence of carbon monoxide additionally introduced to the reaction mixture.

Preferably, in this preferred embodiment, catalyst is pretreated with a gas mixture comprising carbon monoxide and hydrogen and the asymmetric hydrogenation is carried out in the presence of carbon monoxide additionally introduced to the reaction mixture.

The rhodium catalysts soluble in the reaction mixture and used in this preferred embodiment can therefore have at least one CO ligand at least in one form passed through in the catalysis cycle or in a preform upstream of the actual catalysis cycle, it being unimportant here whether this catalyst form having at least one CO ligand is the actual catalytically active catalyst form. In order to stabilize the catalyst forms optionally having CO ligands, it may be advantageous to additionally introduce carbon monoxide to the reaction mixture during the hydrogenation.

In this preferred embodiment, the specified pretreatment of the catalyst precursor is carried out with a gas mixture comprising 20 to 90% by volume carbon monoxide, 10 to 80% by volume hydrogen and 0 to 5% by volume further gases, where the specified volume fractions add up to 100% by volume, at a pressure of 5 to 100 bar. Additionally, excess carbon monoxide is separated off from the resulting catalyst prior to use in the asymmetric hydrogenation.

The term excess carbon monoxide is to be understood here as meaning the carbon monoxide which is present in the resulting reaction mixture in gaseous or dissolved form and is not bonded to the transition metal catalyst or its precursor. Accordingly, the excess carbon monoxide not bonded to the catalyst is removed at least largely, i.e. to an extent that any residual amounts of dissolved carbon monoxide do not make themselves noticeably disruptive in the subsequent hydrogenation. This is usually ensured if about 90%, preferably about 95% or more of the carbon monoxide used for the preformation are separated off. Preferably, the excess carbon monoxide is removed completely from the catalyst obtained by preformation.

The separation off of the excess carbon monoxide from the resulting catalyst or from the reaction mixture comprising the catalyst can take place in different ways. Preferably, the catalyst or the mixture comprising the catalyst obtained by preformation is decompressed to a pressure of up to about 5 bar (absolute), preferably, specifically when carrying out the preformation in the pressure range from 5 to 10 bar, to a pressure of less than 5 bar (absolute), preferably to a pressure in the range from about 1 bar to about 5 bar, preferably 1 to less than 5 bar, particularly preferably to a pressure in the range from 1 to 3 bar, very particularly preferably to a pressure in the range from about 1 to about 2 bar, particularly preferably to atmospheric pressure, meaning that gaseous, nonbound carbon monoxide escapes from the product of the preformation.

The aforementioned decompression of the preformed catalyst can take place for example using a high-pressure separator, as is known per se to the person skilled in the art. Separators of this type in which the liquid is in the continuous phase are described for example in: Perry's Chemical Engineers' Handbook, 1997, 7th edition, McGraw-Hill, p. 14.95 and 14.96; the prevention of a possible drop entrainment is described on pages 14.87 to 14.90. The decompression of the preformed catalyst can take place in one stage or two stages until the desired pressure in the range from 1 bar to about 5 bar is reached, during which the temperature usually drops to 10 to 40° C.

Alternatively, the separation off of excess carbon monoxide can be achieved by so-called stripping of the catalyst or of the mixture comprising the catalyst with a gas, advantageously with a gas that is inert under the reaction conditions. Here, the term stripping is understood by the person skilled in the art as meaning the introduction of a gas into the catalyst or the reaction mixture comprising the catalyst, as described for example in W. R. A. Vauck, H. A. Müller, Grundoperationen chemischer Verfahrenstechnik [Basic operations of chemical processing technology], Deutscher Verlag für Grundstoffchemie Leipzig, Stuttgart, 10th edition, 1984, page 800. Suitable inert gases which may be mentioned here by way of example are: hydrogen, helium, neon, argon, xenon, nitrogen and/or $CO_2$, preferably hydrogen, nitrogen, argon.

Preferably, the asymmetric hydrogenation is then carried out with hydrogen which has a carbon monoxide content in the range from 50 to 3000 ppm, in particular in the range from 100 to 2000 ppm, specifically in the range from 200 to 1000 ppm and very specifically in the range from 400 to 800 ppm.

If a preforming of the rhodium catalyst is carried out, usually the selected transition metal compound and the selected chiral ligands and if desired the substrate to be hydrogenated asymmetrically are dissolved in a suitable solvent or solution medium that is inert under the reaction conditions, such as, for example, ether, tetrahydrofuran, methyltetrahydrofuran, toluene, xylene, chlorobenzene, octadecanol, biphenyl ether, texanol, Marlotherm, Oxo Oil 9N (hydroformylation products from isomeric octenes, BASF Aktiengesellschaft), citronellal and the like. The substrate to be reacted, the product or any high-boiling by-products produced during the reaction can also serve as solution medium. A gas mixture which comprises hydrogen and carbon monoxide is injected into the resulting solution, advantageously in a suitable pressurized reactor or autoclave, at a pressure of usually about 5 to about 350 bar, preferably from about 20 to about 200 bar and particularly preferably from about 50 to about 100 bar. Preferably, for the preformation a gas mixture is used which comprises about 30 to 99% by volume hydrogen,
1 to 70% by volume carbon monoxide and
0 to 5% by volume further gases, where the data in % by volume must add up to 100% by volume.

For the preformation, particular preference is given to using a gas mixture which comprises about 40 to 80% by volume hydrogen,
20 to 60% by volume carbon monoxide and
0 to 5% by volume further gases, where the data in % by volume must add up to 100% by volume.

A gas mixture particularly preferred for the preformation is so-called synthesis gas, which usually consists to about 35 to 55% by volume of carbon monoxide alongside hydrogen and traces of further gases.

The preformation of the catalyst is usually carried out at temperatures of from about 25° C. to about 100° C., preferably at about 40° C. to about 80° C. If the preformation is carried out in the presence of the substrate to be hydrogenated asymmetrically, the temperature is advantageously selected such that it does not result, to a troublesome extent, in an isomerization of the double bond to be hydrogenated. The preformation is usually terminated after about 1 h to about 24 h, often after about 1 to about 12 h.

Following the optional preformation to be carried out, the asymmetric hydrogenation of the selected substrate is carried out in accordance with the invention. Following a preceding preformation, the selected substrate can generally be successfully carried out with or without the introduction of additional carbon monoxide. If no preformation is carried out, the asymmetric hydrogenation according to the invention can be carried out either in the presence of carbon monoxide introduced into the reaction system or without the introduction of carbon monoxide. Advantageously, a preformation is carried out as described and additional carbon monoxide is added to the reaction mixture during the asymmetric hydrogenation.

If carbon monoxide is introduced into the reaction system, the introduction can be carried out in various ways: thus, for example, the carbon monoxide can be admixed with the hydrogen used for the asymmetric hydrogenation, or else be metered in directly in gaseous form into the reaction solution. A further option consists for example in adding compounds to the reaction mixture which readily release carbon monoxide, such as for example formates or oxalyl compounds.

The carbon monoxide is preferably admixed with the hydrogen used for the asymmetric hydrogenation.

The asymmetric hydrogenation according to the invention is advantageously carried out at a pressure of about 2 to about 200 bar, in particular about 10 to about 100 bar, specifically at about 60 to about 100 bar and a temperature of generally about 0° C. to about 100° C., preferably about 0° C. to about 30° C., in particular at about 10° C. to about 30° C.

The selection of the solvent to be used for carrying out the asymmetric hydrogenation according to the invention is less important. In any case, advantages according to the invention also arise in different solvents. Suitable solvents are, for example, those mentioned for carrying out the preformation according to the invention. With particular advantage, the asymmetric hydrogenation is carried out in the same solvent as the preformation optionally carried out beforehand.

Suitable reaction vessels for carrying out the asymmetric hydrogenation according to the invention are in principle all those which permit reactions under the specified conditions, in particular pressure and temperature, and are suitable for hydrogenation reactions, such as, for example, autoclaves, tubular reactors, bubble columns, etc.

If the hydrogenation of the process according to the invention is carried out using high-boiling, generally viscous solvents, as are described for example above in connection with the use in the course of the pretreatment of the catalyst (for example the specified solvents octadecanol, biphenyl ether, texanol, Marlotherm®, Oxo Oil 9N) or if the hydrogenation is carried out without the additional use of solvents, but with accumulation of the high-boiling components arising as by-products to a low degree (such as, for example, dimers or trimers which are formed by reactions of the starting materials and/or products and subsequent secondary reactions), it may be advantageous to provide good gas introduction and good thorough mixing of gas phase and condensed phase. This is achieved for example by carrying out the hydrogenation step of the process according to the invention in a gas circulation reactor. Gas circulation reactors are known per se to the person skilled in the art and are described for example in P. Trambouze, J.-P. Euzen, Chemical Reactors, Ed. Technip, 2004, p. 280-283 and P. Zehner, R. Benfer, Chem. Eng. Sci. 1996, 51, 1735-1744, and also e.g. in EP 1 140 349. In principle, it is also possible to carry out the reaction in the product as solvent, for example in citronellal when the starting material is neral or geranial.

When using a gas circulation reactor as specified above, it has proven to be particularly advantageous to introduce the gas or gas mixture (hydrogen comprising carbon monoxide) to be used in parallel to the starting materials introduced into the reactor and/or the circulating reaction mixture or the catalyst by means of a single nozzle or a two-material nozzle into the gas circulation reactor. Here, the two-material nozzle is notable for the fact that liquid and gas to be introduced into the reactor arrive through two separate concentric tubes under pressure to the mouth of the nozzle, where they are combined with one another.

The process according to the invention can be successfully carried out with and without the addition of tertiary amines. Preferably, the process according to the invention is carried out in the absence, i.e. without the addition of additional tertiary amines or in the presence of only catalytic amounts of additional tertiary amines. The amount of amine used here can be between 0.5 and 500 mol equivalents, based on the amount of metal used, but is preferably 1 to 100 mol equivalents based on the amount of metal used. The choice of tertiary amine is not critical. As well as short-chain alkylamines, such as, for example, triethylamine, it is also possible to use long-chain alkylamines, such as for example tridodecylamine. In the context of a preferred embodiment, the hydrogenation process according to the invention is carried out in the presence of a tertiary amine, preferably tridodecylamine, in an amount of about 2 to 30 mol equivalents, preferably about 5 to 20 mol equivalents and particularly preferably 5 to 15 mol equivalents, based on the amount of transition metal used.

The reaction is advantageously terminated when the target compound is present in the desired yield and the desired optical activity, i.e. with the desired enantiomer excess (ee) in the reaction mixture, as can be established by the person skilled in the art by means of routine experiments for example by means of chromatographic methods. Usually, the hydrogenation is terminated after about 1 to about 150 h, often after about 2 to about 24 h.

By means of the process according to the invention it is possible to provide optically active carbonyl compounds, in particular optically active aldehydes, in high yields and enantiomer excesses. Usually, the desired asymmetrically hydrogenated compounds are obtained in an enantiomer excess of at least 80% ee, often with an enantiomer excess with about 85 to about 99% ee. In this connection, it is to be noted that the maximum achievable enantiomer excess may depend on the purity of the substrate used, in particular with regard to the isomer purity of the double bond to be hydrogenated.

Consequently, suitable starting substances are in particular those which have an isomer ratio of at least about 90:10, preferably at least about 95:5 with regard to the E/Z double-bond isomers.

By means of the preforming and/or by means of the carbon monoxide additionally introduced into the reaction system, the homogeneous catalysts used can be stabilized, as a result of which, on the one hand, the service life of the catalysts is considerably increased and, on the other hand, the reusability of the homogeneous catalysts is facilitated.

Thus, for example, the resulting reaction product can be removed from the reaction mixture by processes known per se to the person skilled in the art, such as e.g. by distillation, and the catalyst that is left behind can be used in the course of further reactions, optionally after repeated preformation.

The process according to the invention can accordingly be operated either discontinuously or semicontinuously as well as continuously and is suitable in particular for reactions on an industrial scale.

In the context of a particularly preferred embodiment of the process according to the invention, neral or geranial, which comprises up to about 5 mol %, preferably up to about 2 mol %, of the respective double-bond isomers, is converted to optically active citronellal. To form the catalyst, preference is given to using a rhodium compound that is soluble in the reaction mixture, in particular $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$, $Rh_2(OAc)_4$, bis(ethylene)rhodium(I) acetylacetonate or $Rh_6(CO)_{16}$ and as chiral ligand (R,R)-chiraphos or (S,S)-chiraphos ((2R, 3R)-(+)-2,3-bis(diphenylphosphino)butane or (2S, 3S)-(−)-2,3-bis(diphenyl-phosphino)butane) in the molar ratio of about 1:1 to about 1:4, where the reaction mixture during the hydrogenation of neral or geranial additionally comprises at least one compound of the general formula (I), which is selected in particular from one of the aforementioned compounds (I-1) to (I-12) and specifically from (R,R-chiraphos monoxide, (S,S)-chiraphos monoxide, cyclohexyldiphenylphosphine, cyclopentyldiphenylphosphine, 2-butyldiphenylphosphine or isopropyldiphenylphosphine, wherein the compound of the formula (I) is used in particular in an amount of preferably 0.03 to 0.6 mol per mole of rhodium.

In a particularly preferred embodiment of the process according to the invention, neral which comprises up to about 5 mol %, preferably up to about 2 mol % of geranial is reacted in the presence of a rhodium compound that is soluble in the reaction mixture, such as Rh(OAc)$_3$, [Rh(cod)Cl]$_2$, Rh(CO)$_2$acac, [Rh(cod)OH]$_2$, [Rh(cod)OMe]$_2$, Rh$_4$(CO)$_{12}$, Rh$_2$(OAc)$_4$, bis(ethylene)rhodium(I) acetylacetonate or Rh$_6$(CO)$_{16}$ and (R,R)-chiraphos to give D-citronellal, where the reaction mixture during the hydrogenation additionally comprises at least one compound of the general formula (I), which is selected in particular from one of the aforementioned compounds (I-1) to (I-12) and specifically from (R,R)-chiraphos monoxide, (S,S)-chiraphos monoxide, cyclohexyldiphenylphosphine, cyclopentyldiphenylphosphine, 2-butyldiphenylphosphine or isopropyldiphenylphosphine, wherein the compound of the formula (I) is used in particular in an amount of from 0.03 to 0.6 mol per mole of rhodium. In another likewise particularly preferred embodiment of the process according to the invention, neral which comprises up to about 5 mol %, preferably up to about 2 mol % geranial is reacted in the presence of a rhodium compound that is soluble in the reaction mixture, such as Rh(OAc)$_3$, [Rh(cod)Cl]$_2$, Rh(CO)$_2$acac, [Rh(cod)OH]$_2$, [Rh(cod)OMe]$_2$, Rh$_4$(CO)$_{12}$, Rh$_2$(OAc)$_4$, bis(ethylene)rhodium(I) acetylacetonate or Rh$_6$(CO)$_{16}$ and (S,S)-chiraphos to give L-citronellal, where the reaction mixture during the hydrogenation additionally comprises at least one compound of the general formula (I), which is selected in particular from one of the aforementioned compounds (I-1) to (I-12) and specifically from (R,R)-chiraphos monoxide, (S,S)-chiraphos monoxide, cyclohexyldiphenylphosphine, cyclopentyldiphenylphosphine, 2-butyldiphenylphosphine or isopropyldiphenylphosphine, wherein the compound of the formula (I) is used in particular in an amount of from 0.03 to 0.6 mol per mole of rhodium. Preferably, the catalyst is preformed under the conditions mentioned above and then the asymmetric hydrogenation is carried out in the presence of hydrogen which comprises in particular 50 to 3000 ppm of carbon monoxide. In the course of the preferred embodiment, the addition of solvents is advantageously dispensed with and the stated conversions are carried out in the substrate to be reacted or the product and optionally in high-boiling byproducts as dissolution medium. Of particular preference is the continuous reaction procedure with reuse or recycling of the homogeneous catalyst stabilized according to the invention.

In principle, it is possible to replace (R,R)-chiraphos with (R,R)-norphos ((2R,3R)-2,3-bis(diphenylphosphino)bicyclo[2.2.1]hept-4-ene) or (S,S)-chiraphos with (S,S)-norphos ((2S,3S)-2,3-bis(diphenylphosphino)bicyclo[2.2.1]hept-4-ene).

A further aspect of the present invention relates to a process for the preparation of optically active menthol using optically active citronellal prepared by the process according to the invention. The preparation of optically active menthol proceeding from optically active citronellal is known. A key step here is the cyclization of optically active citronellal to optically active isopulegol, as described for example in EP-A 1 225 163.

The process for the preparation of optically active menthol comprises the following steps:
i) preparation of optically active citronellal by asymmetric hydrogenation of geranial of the formula (IIa-1) or of neral of the formula (IIb-1) by the process according to the invention,
ii) cyclization of the optically active citronellal prepared in this way to give optically active isopulegol in the presence of a Lewis acid and
iii) hydrogenation of the optically active isopulegol prepared in this way to give optically active menthol.

As shown below in diagrammatic form for the preparation of L-menthol of the formula (XIII), the optically active citronellal prepared according to the invention can be cyclized in the presence of a suitable acid, in particular a Lewis acid to give L-isopulegol of the formula (XII) and then hydrogenated to L-menthol.

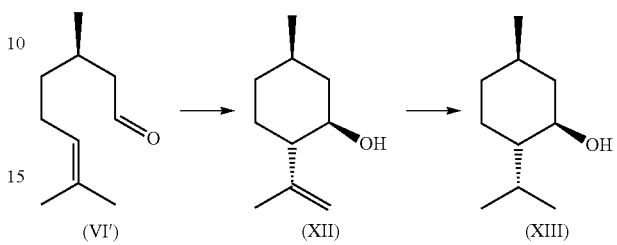

A further aspect of the present invention accordingly relates to the use of optically active citronellal prepared by the process according to the invention for preparing optically active menthol. In particular, the invention relates to the use of the D-citronellal prepared by the process according to the invention for preparing optically active L-menthol.

The examples below serve to illustrate the invention without adversely affecting it in any way:

EXAMPLES

Comparative Example 1: Asymmetric Hydrogenation of Neral in the Presence of Carbon Monoxide Rh(CO)$_2$acac (43 mg, 0.17 mmol) and (R,R)-chiraphos (105 mg, 0.24 mmol) were dissolved in texanol (28 ml, 2,2,4-trimethyl-1,3-pentanediol monoisobutyrate, Sigma-Aldrich) and stirred in a 100 ml steel autoclave (V2A steel, manufacturer Premex, magnetically coupled gas-dispersion stirrer, 1000 revolutions/min) at 80 bar synthesis gas (H$_2$/CO=1:1, vol./vol.) and 70° C. for 16 h. The system is then cooled to 25° C. and nitrogen is passed through the solution for two hours (8 l/h). After flushing with nitrogen, neral (16.2 g, ratio of the double-bond isomers neral/geranial=98.3:0.4; molar ratio substrate/catalyst=650) was added to the autoclave via a lock. The reaction pressure was adjusted to 80 bar by injecting hydrogen gas which comprised 1000 ppm of carbon monoxide. Time/conversion was determined by gas chromatography. After a reaction time of 4 hours, a conversion of 319% was achieved and a yield of 39% of citronellal. After 20 h, the conversion of citral was >99% and the yield of D-citronellal was likewise >99%, with the optical purity being determined as 85% ee.

Examples 2a-2o: Asymmetric Hydrogenation of Neral in the Presence of Carbon Monoxide with the Addition of a Promoter (Table 1) at c(Rh)=400 ppm Rh(CO)$_2$acac (43 mg, 0.17 mmol), (R,R)-chiraphos (105 mg, 0.24 mmol) and an additive (see table 1) were dissolved in texanol (28 ml, 2,2,4-trimethyl-1,3-pentanediol monoisobutyrate, Sigma-Aldrich) and stirred in a 100 ml steel autoclave (V2A steel, manufacturer Premex, magnetically coupled gas-dispersion stirrer, 1000 revolutions/min) at 80 bar synthesis gas (H$_2$/CO=1:1, vol./vol.) and 70° C. for 16 h. Then, the system is cooled to 25° C. and nitrogen is passed through the solution for two hours (8 l/h). After flushing with nitrogen, 16.2 g of neral (ratio of the double-bond isomers neral/geranial=98.3:0.4; ratio substrate/catalyst=650) were added to the autoclave via a lock. The reaction pressure was adjusted to 80 bar by injecting hydrogen gas which comprised 1000 ppm of carbon monoxide. Time/conversion was determined by gas chromatography. Conversions/enantioselectivities/additives are given in table 1.

Examples 2p-q: Asymmetric Hydrogenation of Neral in the Presence of Carbon Monoxide with the Addition of a Promoter (Table 1) at c(Rh)=700 ppm $Rh(CO)_2acac$ (75 mg, 0.29 mmol), (R,R)-chiraphos (186 mg, 0.44 mmol) and an additive (see table 1) were dissolved in texanol (28 ml, 2,2,4-trimethyl-1,3-pentanediol monoisobutyrate, Sigma-Aldrich) and stirred in a 100 ml steel autoclave (V2A steel, manufacturer Premex, magnetically coupled gas-dispersion stirrer, 1000 revolutions/min) at 80 bar synthesis gas ($H_2$/CO=1:1, vol./vol.) and 70° C. for 16 h. Then, the system is cooled to 25° C. and nitrogen is passed through the solution for two hours (8 l/h). After flushing with nitrogen, 16.2 g of neral (ratio of the double-bond isomers neral/geranial=98.3:0.4; ratio substrate/catalyst=365) were added to the autoclave via a lock. The reaction pressure was adjusted to 80 bar by injecting hydrogen gas which comprised 1000 ppm of carbon monoxide. Time/conversion was determined by gas chromatography. Conversions/enantioselectivities/additives are given in table 1.

Comparative Example, 2r-s: Asymmetric Hydrogenation of Neral in the Presence of Carbon Monoxide with the Addition of the Promoter without Bidentate Ligands (Table 1) at c(Rh)=400 ppm $Rh(CO)_2acac$ (43 mg, 0.17 mmol) and the phosphine ligand (0.17 mmol, see table 1) were dissolved in texanol (28 ml, 2,2,4-trimethyl-1,3-pentanediol monoisobutyrate, Sigma-Aldrich) and stirred in a 100 ml steel autoclave (V2A steel, manufacturer Premex, magnetically coupled gas-dispersion stirrer, 1000 revolutions/min) at 80 bar synthesis gas ($H_2$/CO=1:1, vol./vol.) and 70'C for 16 h. Then, the system is cooled to 25° C. and nitrogen is passed through the solution for two hours (8 l/h). After flushing with nitrogen, 16.2 g of neral (ratio of the double-bond isomers neral/geranial=98.3:0.4; ratio substrate/catalyst=650) were added to the autoclave via a lock. The reaction pressure was adjusted to 80 bar by injecting hydrogen gas which comprised 1000 ppm of carbon monoxide. Time/conversion was determined by gas chromatography. Conversions and enantioselectivities are given in table 1.

Comparative Example 2t

The reaction were carried out according to the procedure described for example 2b, replacing the solvent texanol with the same amount of D-citronellal (88% ee) and adding no (R,R)-chiraphos monoxide as additive to the reaction mixture. Conversions and enantioselectivities are given in table 1.

Example 2u

The reaction were carried out according to the procedure described for example 2b, replacing the solvent texanol with the same amount of D-citronellal (88% ee). Conversions and enantioselectivities are given in table 1.

Comparative Example 2v

The reaction were carried out according to the procedure described for example 2b, replacing (R,R)-chiraphos with the same amount of (R,R)-norphos and adding no (R,R)-chiraphos monoxide as additive to the reaction mixture. Conversions and enantioselectivities are given in table 1.

Example 2w

The reaction were carried out according to the procedure described for example 2b, replacing (R,R)-chiraphos with the same amount of (R,R)-norphos. Conversions and enantioselectivities are given in table 1.

Example 2x

The reaction were carried out according to the procedure described for example 2b, using pure hydrogen instead of the carbon monoxide-containing hydrogen. Conversions and enantioselectivities are given in table 1.

Comparative Example 2y

The reaction were carried out according to the procedure described for example 2a, adding 1.05 mmol of tridodecylamine as additive to the reaction mixture. Conversions and enantioselectivities are given in table 1.

Example 2z

The reaction were carried out according to the procedure described for example 2y, adding (R,R)-chiraphos monoxide as additive to the reaction mixture in addition to the tridodecylamine. Conversions and enantioselectivities are given in table 1.

Example 3: Preparation of (R,R)-Chiraphos Monoxide (CPMO) by Oxidation of (R,R)-Chiraphos with Hydrogen Peroxide (R,R)-Chiraphos (230 g, 0.54 mol) is dissolved, with stirring, in a 5 L jacketed stirring vessel at 25° C. in toluene (3500 mL), and hydrogen peroxide (15% strength in water, 9 g, 0.26 mol) is continuously added over the course of 8 hours via an injection pump. The temperature is kept at 25° C. (the temperature increase caused by exothermy is minimal). The reaction is further stirred overnight for a further 10 hours at 25° C. The reaction discharge is concentrated to 900 ml (clear yellowish solution) on a rotary evaporator at 150 mbar and 75° C. 100 ml of the concentrated solution are concentrated completely at 75° C./5 mbar and purified in the glovebox over a 10*10 cm silica gel column. To separate off unreacted chiraphos, firstly elution with toluene is carried out (1500 mL), then with methanol (600 mL), control of the fractions by means of GC (column: 30 m/0.32 mm HP-5; injector: 280° C., detector: FID; 320° C., program: 100° C.→20° C./min→300° C.). 3.1 g of a mixture of CPMO: CPDO=76:24 (based on $^{31}$P-NMR) are obtained. $^{31}$P-NMR ($C_6D_6$, 500 MHz): 33.5 ppm (CPDO), 33.0 ppm (d, 30 Hz), −8.1 ppm (d, 30 Hz)

TABLE 1

Overview of the results of examples 1 and 2a-s

| Example | Compound (I)[a] [mmol] | mol % based on chiraphos | c (Rh, total) [ppm] | 4 h [%][e] | 20 h [%][f] | % ee |
|---|---|---|---|---|---|---|
| 1*) | — | — | 400 | 39 | >99 | 85 |
| 2a | CPMO[b] (0.066) | 26% | 400 | 93 | >99 | 87 |
| 2b | CPMO[b] (0.075) | 30% | 400 | 97 | >99 | 87 |
| 2c*) | TPP (0.028) | 10% | 400 | 45 | 98 | 85 |
| 2d*) | TPP (0.081) | 30% | 400 | 44 | >99 | 87 |
| 2e | CyDPP (0.026) | 10% | 400 | 68 | >99 | 85 |
| 2f | CyDPP (0.077) | 30% | 400 | 98 | >99 | 87 |
| 2g | iPrDPP (0.028) | 10% | 400 | 57 | 97 | 84 |
| 2h | iPrDPP (0.076) | 30% | 400 | 95 | >99 | 87 |
| 2i*) | HexDPP (0.025) | 10% | 400 | 34 | 99 | 83 |
| 2j*) | HexDPP (0.076) | 30% | 400 | 33 | >99 | 87 |
| 2k | CPMO[b] (0.024) | 10% | 400 | 55 | >99 | 87 |
| 2l | CPMO[b] (0.034) | 15% | 400 | 84 | >99 | 87 |
| 2m*) | DPPE-O | 10% | 400 | 28 | 98 | 83 |
| 2n*) | DPPE-O | 30% | 400 | 26 | 98 | 85 |
| 2o*) | CPDO | 30% | 400 | 23 | >99 | 84 |
| 2p*) | — | — | 700 | 75 | >99 | 87 |
| 2q | CPMO[b] (0.130) | 30% | 700 | >99 | >99 | 87 |
| 2r*) | only CPMO[b] | CMPO:Rh = 1:1 | 400 | 1 | 1 | n.d.[d] |
| 2s*) | only iPrDPP | iPrDPP:Rh = 1:1 | 400 | 4 | 6 | n.d.[d] |
| 2t*)g) | — | — | 400 | 68 | >99 | 89 |
| 2u g) | CPMO[b] (0.075) | 30% | 400 | 79 | >99 | 89 |
| 2v*)h) | — | — | 400 | 14 | 70 | 83 |
| 2w h) | CPMO[b] (0.075) | 30% | 400 | 41 | 95 | 84 |
| 2x i) | CPMO[b] (0.075) | 30% | 400 | 88 | 98 | 87 |
| 2y*) | Tridodecylamine (1.05) | 400% | 400 | 54 | 99 | 86 |
| 2z | Tridodecylamine (1.05) CPMO[b] (0.075) | 400% 30% | 400 | 97 | 99 | 86 |

*) The examples marked with an asterisk are comparative examples.
[a] See table 2;
[b] CPMO was added as a mixture of 75% CPMO with 23% CPDO (preparation corresponding to example 3); the added amount refers to the added amount of pure CPMO in this mixture;
[d] not determined, too low a conversion;
[e] conversion after 4 h;
[f] conversion after 20 h;
[g] the solvent texanol was replaced with D-citronellal (88% ee);
[h] (R,R)-chiraphos was replaced with (R,R)-norphos;
[i] introduced hydrogen comprises no CO.

TABLE 2

Ligand structures

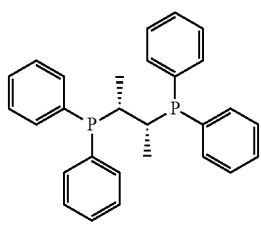 [SMILES: C[C@H]([C@@H](C)P(c1ccccc1)c1ccccc1)P(c1ccccc1)c1ccccc1]

(R,R)-Chiraphos
(CAS 74839-84-2)

TABLE 2-continued

Ligand structures

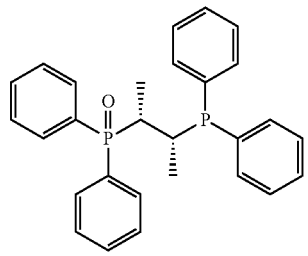 [SMILES: C[C@H]([C@@H](C)P(=O)(c1ccccc1)c1ccccc1)P(c1ccccc1)c1ccccc1]

(R,R)-Chiraphos monoxide
(CPMO, no CAS assigned)

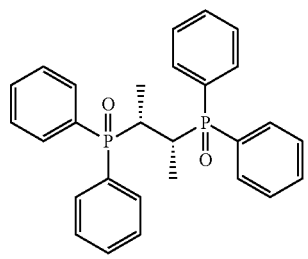 [SMILES: C[C@H]([C@@H](C)P(=O)(c1ccccc1)c1ccccc1)P(=O)(c1ccccc1)c1ccccc1]

(R,R)-Chiraphos dioxide
(CPDO, CAS 192449-15-3)

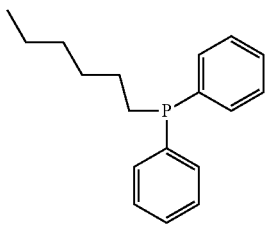 [SMILES: CCCCCCP(c1ccccc1)c1ccccc1]

Hexyldiphenylphosphine
(HexylDPP, CAS 18298-00-5)

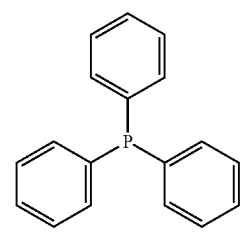 [SMILES: c1ccc(P(c2ccccc2)c2ccccc2)cc1]

Triphenylphosphine (TPP, CAS 603-35-0)

TABLE 2-continued

Ligand structures

Cyclohexyldiphenyl-
phosphine (CyDPP,
CAS 6372-42-5)

Isopropyldiphenyl-
phosphine (iPrDPP,
CAS 6372-40-3)

1,2-Bis(diphenyl-
phosphine)ethane
monoxide (DPPE-
O, CAS 984-43-0,
Sigma-Aldrich)

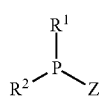

(R,R)-norphos
CAS 71042-55-2-

The invention claimed is:

1. A composition comprising a chiral bidentate bisphosphine ligand and at least one compound of the general formula (I):

(I)

in which $R^1$ and $R^2$: are identical or different and are $C_6$- to $C_{10}$-aryl which is unsubstituted or carries one or more substituents which are selected from $C_1$- to $C_6$-alkyl, $C_3$- to $C_6$-cycloalkyl, $C_6$- to $C_{10}$-aryl, $C_1$- to $C_6$-alkoxy and amino;

Z is a group $CHR^3R^4$ or aryl which is unsubstituted or carries one or more substituents which are selected from $C_1$- to $C_6$-alkyl, $C_3$- to $C_6$-cycloalkyl, $C_6$- to $C_{10}$-aryl, $C_1$- to $C_6$-alkoxy and amino, in which $R^3$ is $C_1$- to $C_4$-alkyl, $C_1$- to $C_4$-alkoxy-$C_1$- to $C_4$-alkyl, $C_3$- to $C_6$-cycloalkyl or $C_6$- to $C_{10}$-aryl, where one or two nonadjacent $CH_2$ groups in $C_3$- to $C_6$-cycloalkyl can also be replaced by an oxygen atom;

$R^4$ is $C_1$- to $C_4$-alkyl which is unsubstituted or carries a group $P(=O)R^{4a}R^{4b}$, $C_1$- to $C_4$-alkoxy, $C_1$- to $C_4$-alkoxy-$C_1$- to $C_4$-alkyl, $C_3$- to $C_6$-cycloalkyl or $C_6$- to $C_{10}$-aryl, where one or two nonadjacent $CH_2$ groups in $C_3$- to $C_6$-cycloalkyl can also be replaced by an oxygen atom, and where $C_3$- to $C_6$-cycloalkyl and $C_6$- to $C_{10}$-aryl are unsubstituted or carry one or more substituents which are selected from $C_1$- to $C_4$-alkyl, $C_1$- to $C_4$-alkoxy and amino;

or $R^3$ and $R^4$: together with the carbon atom to which they are bonded, are $C_4$- to $C_8$-cycloalkyl, in which one or two nonadjacent $CH_2$ groups in $C_3$- to $C_6$-cycloalkyl can also be replaced by an oxygen atom and where $C_3$- to $C_6$-cycloalkyl is unsubstituted or carries one or more substituents which are selected from $C_1$- to $C_4$-alkyl, $C_1$- to $C_4$-alkoxy and A-$P(=O)R^{4a}R^{4b}$, where A is a chemical bond or a $C_1$- to $C_4$-alkylene; and $R^{4a}$ and $R^{4b}$: are identical or different and are phenyl which is unsubstituted or carries one or more substituents which are selected from $C_1$- to $C_6$-alkyl, $C_3$- to $C_6$-cycloalkyl, $C_6$- to $C_{10}$-aryl, $C_1$- to $C_6$-alkoxy and amino.

2. The composition of claim 1, wherein Z in formula (I) is a group $CHR^3R^4$.

3. The composition of claim 2, wherein the variables $R^1$, $R^2$, Z in formula (I) have the following meanings:

$R^1$, $R^2$: are identical or different and are phenyl which is unsubstituted or carries 1, 2 or 3 substituents which are selected from methyl and methoxy;

Z is a group $CHR^3R^4$, in which $R^3$ is $C_1$- to $C_4$-alkyl;

$R^4$ is $C_1$- to $C_4$-alkyl which is unsubstituted or carries a group $P(=O)R^{4a}R^{4b}$;

or $R^3$, $R^4$: together with the carbon atom to which they are bonded, is $C_3$- to $C_8$-cycloalkyl in which one or two $CH_2$ groups can be replaced by one or two oxygen atoms and where $C_3$- to $C_6$-cycloalkyl is unsubstituted or carries a group A-$P(=O)R^{4a}R^{4b}$ and/or has 1, 2, 3 or 4 methyl groups as substituents;

where A is a chemical bond, $CH_2$ or $CH(CH_3)$; and $R^{4a}$ and $R^{4b}$: are identical or different and are $C_6$- to $C_{10}$-aryl which is unsubstituted or carries 1, 2 or 3 substituents which are selected from methyl and methoxy.

4. The composition of claim 2, in which $R^1$, $R^2$: are unsubstituted phenyl;

$R^3$ is methyl;

$R^4$ is a group $CH(CH_3)$—$P(=O)R^{4a}R^{4b}$ in which $R^{4a}$ and $R^{4b}$ are in each case unsubstituted phenyl.

5. The composition of claim 1, wherein the chiral, bidentate bisphosphine ligand is a compound of the general formulae (IX), (X) or (XI):

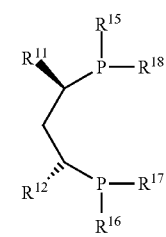

(IX)

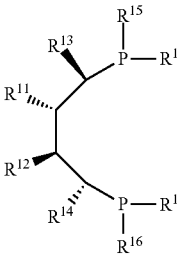

(X)

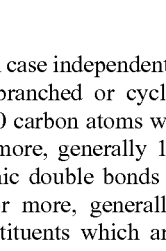

(XI)

in which
- $R^{11}$, $R^{12}$: in each case independently of one another are an unbranched, branched or cyclic hydrocarbon radical having 1 to 20 carbon atoms which is saturated or can have one or more, generally 1 to about 4, nonconjugated, ethylenic double bonds and is unsubstituted or carries one or more, generally 1 to 4, identical or different substituents which are selected from $OR^{19}$, $NR^{20}R^{21}$, halogen, $C_6$-$C_{10}$-aryl and $C_3$-$C_9$-hetaryl, or $R^{11}$ and $R^{12}$ together can also be a 2 to 10-membered alkylene group or a 3- to 10-membered cycloalkylene group, in which 1, 2, 3 or 4 nonadjacent $CH_2$ groups can be replaced by O or N—$R^{9c}$, where the alkylene group and the cycloalkylene group are saturated or have one or two nonconjugated ethylenic double bonds, and where the alkylene group and the cycloalkylene group are unsubstituted or carry one or more identical or different substituents which are selected from $C_1$- to $C_4$-alkyl;
- $R^{13}$, $R^{14}$: are in each case independently of one another hydrogen or straight-chain or branched $C_1$- to $C_4$-alkyl and
- $R^{15}$, $R^{16}$, $R^{17}$, $R^{18}$: are identical or different and are $C_6$- to $C_{10}$-aryl which is unsubstituted or carries one or more substituents which are selected from $C_1$- to $C_6$-alkyl, $C_3$- to $C_6$-cycloalkyl, $C_6$- to $C_{10}$-aryl, $C_1$- to $C_6$-alkoxy and amino;
- $R^{19}$, $R^{20}$, $R^{21}$: are in each case independently of one another hydrogen, $C_1$-$C_4$-alkyl, $C_6$-$C_{10}$-aryl, $C_7$-$C_{12}$-aralkyl or $C_7$-$C_{12}$-alkylaryl, where
- $R^{20}$, $R^{21}$: can together also be an alkylene chain having 2 to 5 carbon atoms, which can be interrupted by N or O.

6. The composition of claim 5, wherein the chiral, bidentate bisphosphine ligand is a compound of the general formula (IX).

7. The composition of claim 6, wherein the chiral, bidentate bisphosphine ligand is either the compound of the formula (IXa) or the formula (IXb):

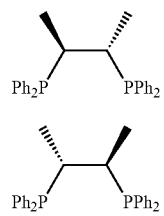

(IXa)

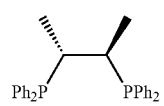

(IXb)

in which Ph is phenyl.

8. The composition of claim 6, wherein the chiral, bidentate bisphosphine ligand is either the compound of the formula (IXc) or the formula (IXd):

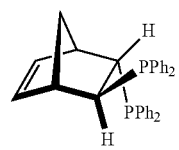

(IXd)

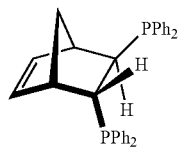

(IXd)

in which Ph is phenyl.

9. The composition of claim 1, where the compound of formula (I) is (2-(diphenylphosphoryl)-1-methylpropyl))diphenylphosphane.

10. The composition of claim 1, where the compound of formula (I) is one of the compounds of formulae (I-1a) or (I-1b) or the racemate thereof

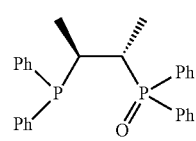

(I-1a)

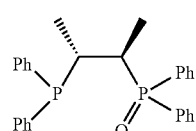

(I-1b)

in which Ph is phenyl, and the racemate thereof.

11. The composition of claim 6, where the compound of formula (I) is (2-(diphenylphosphoryl)-1-methylpropyl))diphenylphosphane.

12. The composition of claim 6, where the compound of formula (I) is one of the compounds of formulae (I-1a) or (I-1b) or the racemate thereof

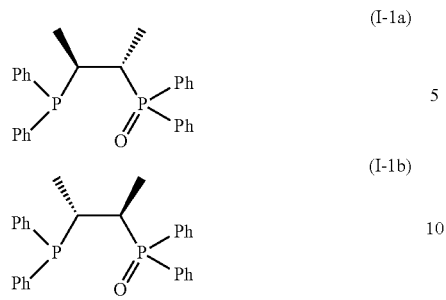
(I-1a)
(I-1b)
in which Ph is phenyl, and the racemate thereof.
13. The composition of claim 11, further comprising a transition metal compound, which contains rhodium as transition metal.
14. The composition of claim 1, further comprising a transition metal compound, which contains rhodium as transition metal.
* * * * *